(12) United States Patent
Singhatat et al.

(10) Patent No.: US 8,388,690 B2
(45) Date of Patent: Mar. 5, 2013

(54) OSTEOTOMY SYSTEM

(75) Inventors: Wamis Singhatat, Santa Ana, CA (US); Giuseppe Lombardo, New Port Richey, FL (US); Drew Amery, Clearwater, FL (US)

(73) Assignee: Linvatec Corporation, Largo, FL (US)

( * ) Notice: Subject to any disclaimer, the term of this patent is extended or adjusted under 35 U.S.C. 154(b) by 1561 days.

(21) Appl. No.: 10/958,036

(22) Filed: Oct. 4, 2004

(65) Prior Publication Data
US 2005/0075641 A1  Apr. 7, 2005

Related U.S. Application Data

(60) Provisional application No. 60/508,779, filed on Oct. 3, 2003.

(51) Int. Cl.
*A61F 2/28* (2006.01)
*A61F 2/46* (2006.01)
*A61B 17/68* (2006.01)
*A61B 17/90* (2006.01)

(52) U.S. Cl. ............. 623/23.51; 623/20.16; 606/87

(58) Field of Classification Search .......... 623/16.11, 623/20.16, 17.11, 17; 606/87
See application file for complete search history.

(56) References Cited

U.S. PATENT DOCUMENTS

| | | | |
|---|---|---|---|
| 4,759,351 A * | 7/1988 | Slocum | 606/62 |
| 6,086,593 A * | 7/2000 | Bonutti | 606/87 |
| 6,203,546 B1 * | 3/2001 | MacMahon | 606/87 |
| 6,221,075 B1 * | 4/2001 | Tormala et al. | 606/77 |
| 6,544,266 B1 * | 4/2003 | Roger et al. | 606/70 |
| 2002/0107571 A1 * | 8/2002 | Foley | 623/17.11 |

FOREIGN PATENT DOCUMENTS

| | | | |
|---|---|---|---|
| DE | 200 12 549 U1 | * | 10/2000 |
| EP | 0 834 295 A1 | * | 4/1998 |
| EP | 0 869 753 B1 | * | 7/2000 |
| FR | 2 612 392 A1 | * | 9/1988 |
| FR | 2 727 005 A1 | * | 5/1996 |
| JP | 5-208029 A | * | 8/1993 |
| SU | 1653762 A1 | * | 6/1991 |

OTHER PUBLICATIONS

English language translation of SU 1653762 A1 (published Jun. 7, 1991).*
Article from the Clinical Orthopaedics and Related Research, No. 395, pp. 180-185 entitled Avoidance of Medical Cortical Fracture in High Tibial Osteotomy: Improved Technique.
Written by Oliver C. Kessler, M.D.; Hilaire A.C. Jacob, PHD; and Jose Romero, MD, 2002.

* cited by examiner

*Primary Examiner* — David H. Willse

(57) ABSTRACT

An osteotomy system, typically for tibial alignment correction, includes a wedge implant and an osteotomy guide. The wedge implant is generally U-shaped and its upper and lower surfaces may be inclined with respect to one another in two orthogonal planes to correct respective misalignments. The osteotomy guide controls cutting of the osteotomy opening and the drilling of a hole defining the apex of the osteotomy, forming a bony hinge about which the osteotomy may be opened.

33 Claims, 14 Drawing Sheets

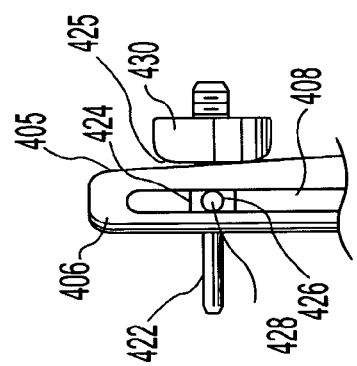
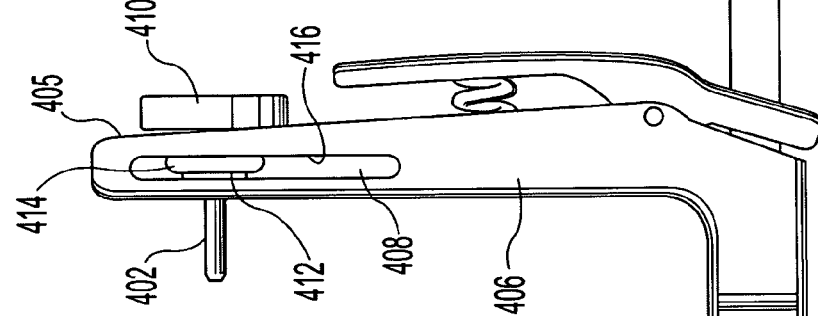
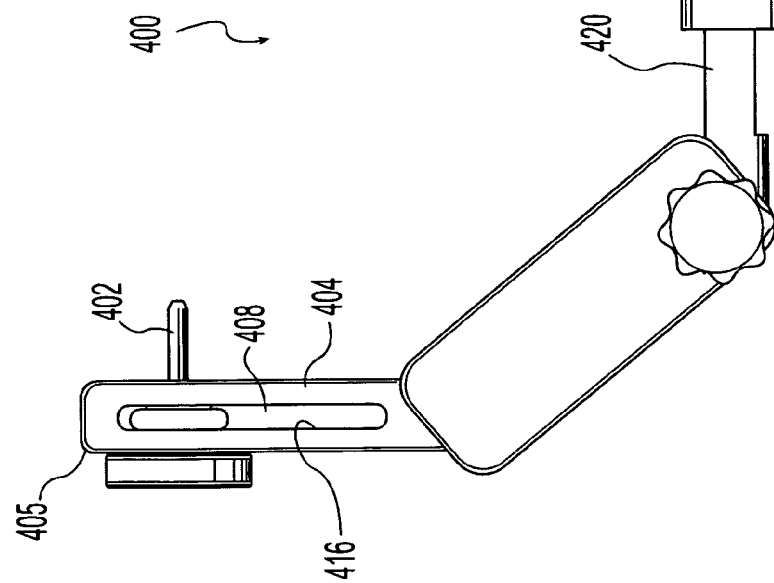
Fig. 18
Fig. 17

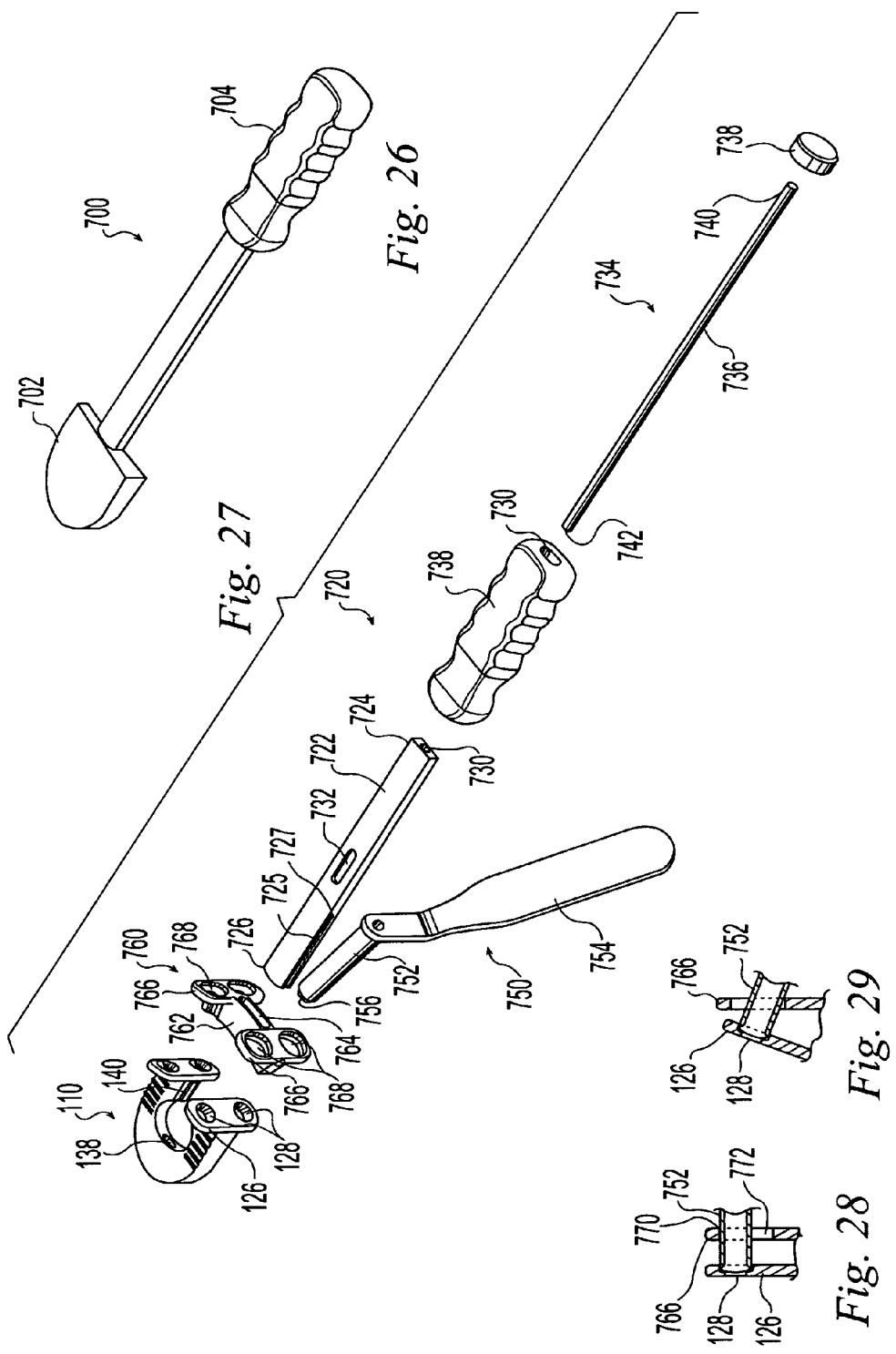

OSTEOTOMY SYSTEM

CROSS-REFERENCE TO RELATED APPLICATIONS

This application claims the benefit of U.S. Provisional Application No. 60/508,779, filed Oct. 3, 2003.

FIELD OF THE INVENTION

The invention relates to an apparatus and procedure for surgically correcting joint alignment. More particularly, the invention relates to an apparatus and procedure for performing an osteotomy to correct knee alignment.

BACKGROUND

A variety of conditions may negatively affect the human knee including arthritis, ligament instability, and localized trauma. These conditions may be surgically treated by repairing portions of the knee cartilage, meniscus, or ligaments or by replacing them with natural or artificial replacements. In such procedures, it is often necessary to correct the alignment of the knee to relieve pressure from the damaged portion of the joint and balance the load on the joint. In some instances, correcting the knee alignment alone, without additional repair or replacement of injured or diseased tissue, is sufficient to provide relief and improve function. Often, in a young arthritis patient, correcting the knee alignment may be a first surgical choice to provide years of relief prior to resorting to a more aggressive total knee replacement procedure. Typically, injured or diseased knees will develop a varus deformity in which the medial side of the person's knee joint has become compressed resulting in a bowlegged alignment of the lower limb.

A frequently used procedure to correct knee alignment is high tibial osteotomy. In this procedure, the knee alignment is changed by cutting the tibia on one side and then expanding or compressing the cut side to change the angle between the axes of the tibia and femur. For example, in a closing high tibial osteotomy, a wedge of bone is removed from the tibia and then the opposite sides of the cut are brought together to angle the tibia towards the side on which the cut was made. In an opening high tibial osteotomy, a cut is made partway across the tibia and the cut is opened to create a wedge-shaped gap thereby angling the tibia away from the side on which the cut was made. A fixturing device, such as a bone plate or external fixator, is then applied to the tibia to hold the tibial alignment until the bone heals. Typically, for opening high tibial osteotomy, bone is taken from the patient's pelvis and applied to the gap in the tibia to aid in bone healing. An opening high tibial osteotomy may be performed on the medial side of a patient's knee to treat a varus deformity.

Another procedure used to correct knee alignment is a distal femoral osteotomy. For example, in an opening lateral distal femoral osteotomy, a cut is made partway across the femur from the lateral side and the cut is opened to create a wedge-shaped gap thereby angling the femur away from the lateral side.

SUMMARY

The present invention provides a high tibial osteotomy (HTO) system including a wedge implant and an osteotomy guide.

In one aspect of the invention, a wedge-shaped spacer for insertion into an osteotomy includes a body having a first surface, a second surface, and an insertion axis. The first and second surfaces are angled relative to one another in a first plane containing the insertion axis by a first angle and the first and second surfaces are angled relative to one another in a second plane perpendicular to the insertion axis by a second angle.

In another aspect of the invention, a wedge-shaped spacer for insertion into an osteotomy includes a body having first and second surfaces and proximal and distal ends. The first and second surfaces are angled relative to one another and from the proximal end toward the distal end. The body includes an opening extending through a portion of the body from near the distal end to near the proximal end and lying between the first and second surfaces over a portion of the length of the opening. The spacer further includes a threaded fastener inserted into the opening and engaging the spacer such that the fastener may be mounted on the bone and threaded into the spacer to translate the spacer distally.

In another aspect of the invention, a wedge-shaped spacer for insertion into an osteotomy includes a body having first and second converging surfaces and proximal and distal sidewalls. The spacer includes an opening from the first surface to the second surface extending to the proximal sidewall to form a gap in the proximal sidewall such that the gap permits bone growth between the two bone portions at the proximal opening of the osteotomy.

In another aspect of the invention, a wedge-shaped spacer for insertion into an osteotomy includes a body having a first surface, a second surface, a proximal end, and a distal end. The first and second surfaces converge from the proximal end toward the distal end. The spacer body includes a plurality of zones including one or more bioresorbable materials. The zones have different rates of bioresorption.

In another aspect of the invention, a wedge-shaped spacer for insertion into an osteotomy includes a body having a first surface, a second surface, a proximal end, and a distal end. The first and second surfaces are spaced further apart at a position adjacent to the proximal end than at a position adjacent to the distal end. At least one fixation plate extends from the proximal end transversely to the first and second surfaces. The fixation plate includes at least one transverse hole configured to receive a bone screw and the fixation plate is formed from a relatively more malleable material than the spacer body.

In another aspect of the invention, a wedge-shaped spacer for insertion into an osteotomy formed in a bone includes a body having first and second surfaces and proximal and distal ends. The first and second surfaces converge from the proximal end toward the distal end. The body includes a portal extending through a portion of the body from near the proximal end to the distal end and lying generally between the first and second surfaces. An inserter includes a shaft having a proximal end and a distal end. The inserter shaft includes an axial bore extending from the proximal end to the distal end. The distal end of the inserter shaft is engageable with the proximal end of the spacer in force transmitting relationship. A plunger engages the axial bore of the inserter shaft and is operable to expel material from the distal end of the inserter shaft into the portal in the spacer.

An inserter for inserting a wedge-shaped spacer into an osteotomy formed in a bone includes a shaft having a proximal end and a distal end. The distal end is engageable with the spacer in force transmitting relationship. A drill sleeve guide includes a body mountable on the shaft and an elongated tab extending outwardly away from the drill sleeve guide body generally parallel to the fixation plate. The tab includes an elongated through hole having a vertically oriented long axis.

The vertical dimension of the elongated through hole is greater than the vertical dimension of the fixation plate through hole. A drill sleeve has a proximal end, a distal end, and a longitudinal through bore. The longitudinal through bore is sized to guide a drill. The drill sleeve is extendable through the elongated through hole of the drill sleeve guide such that the distal end of the drill sleeve engages the fixation plate through hole. The drill sleeve is then pivotable between a first angular position in which it abuts the top of the elongated through hole of the drill sleeve guide and the drill sleeve bore is normal to the fixation plate and a second angular position in which it abuts the bottom of the elongated through hole of the drill sleeve guide and the drill sleeve is directed at an angle away from the spacer body such that the drill sleeve can be angled to remain normal to the fixation plate if the fixation plate is bent toward the drill sleeve guide.

In another aspect of the invention, an osteotomy guide for guiding the creation of an osteotomy in a bone includes a first clamping arm, a second clamping arm, and a cutter guide. The second clamping arm opposes the first clamping arm and is mounted to the first clamping arm for relative translation. The arms are translatable between a first position in which they are spaced from opposite sides of the bone and a second position in which they abut opposite sides of the bone in clamping arrangement. The cutter is mounted to one of the first and second arms such that the cutter guide can guide a cutter to form the osteotomy in the bone at a predetermined orientation relative to the first and second clamping arms.

In another aspect of the invention, an osteotomy guide includes a base having means for mounting it on the bone, a cutter guide, a drill guide, and a drill. The cutter guide is mounted to the base such that the cutter guide can guide a cutter to form the osteotomy in the bone at a predetermined orientation relative to the base. The drill guide is mounted to the base and includes a guide bore. The drill is received in the guide bore such that the drill guide can guide the drill to form a hole in the bone at the vertex of the osteotomy.

In another aspect of the invention, a method of correcting the angular alignment of a bone includes: creating an osteotomy in a bone in which the osteotomy partially divides the bone into two bone portions connected by a bony hinge, the osteotomy having a proximal opening at a cortical surface of the bone and a distal vertex adjacent the bony hinge; determining a required first angular correction in a first plane; determining a required second angular correction in a second plane; providing a wedge-shaped spacer comprising a body having first and second surfaces, the first and second surfaces being angled relative to one another in a third plane containing the insertion axis by a third angle, the first and second surfaces being angled relative to one another in a fourth plane by a fourth angle; and inserting the spacer into the osteotomy to simultaneously correct the bone alignment in the first and second planes.

In another aspect of the invention, a method of correcting the angular alignment of a bone includes: creating an osteotomy in a bone in which the osteotomy partially divides the bone into two bone portions connected by a bony hinge, the osteotomy having a proximal opening at a cortical surface of the bone and a distal vertex adjacent the bony hinge; determining at least one required angular correction in a first plane; providing a wedge-shaped spacer comprising a body having first and second surfaces, the first and second surfaces being angled relative to one another in a first plane containing the insertion axis by a first angle different from the value of the predetermined angular correction, the first and second surfaces being angled relative to one another in a second plane perpendicular to the insertion axis by a second angle different from the value of the predetermined angular correction; and inserting the spacer into the osteotomy obliquely such that bone alignment is corrected by the predetermined angular correction as a result of the combined effects of the first and second spacer angles.

In another aspect of the invention, a method of correcting the angular alignment of a bone includes mounting a guide base on the bone; guiding a drill relative to the guide base to create a bone hole at a desired vertex for the angular correction; guiding a cutter relative to the guide base to create an osteotomy in the bone extending from a cortical surface of the bone to the bone hole; and opening the osteotomy to correct the angular alignment of the bone.

In another aspect of the invention, a method of correcting the angular alignment of a bone includes creating an osteotomy in a bone in which the osteotomy partially divides the bone into two bone portions connected by a bony hinge, the osteotomy having a proximal opening at a cortical surface of the bone and a distal vertex adjacent the bony hinge; engaging a wedge-shaped implant with an insertion tool; inserting the implant into the osteotomy with the insertion tool; and using the insertion tool as a syringe to inject bone growth promoting substances through the implant and into the vertex of the osteotomy.

In another aspect of the invention, a method of correcting the angular alignment of a bone includes: creating an osteotomy in a bone in which the osteotomy partially divides the bone into two bone portions connected by a bony hinge, the osteotomy having a proximal opening at a cortical surface of the bone and a distal vertex adjacent the bony hinge; inserting a wedge-shaped spacer into the osteotomy, the spacer comprising a body having first and second surfaces and proximal and distal sidewalls, the first and second surfaces being angled relative to one another in a first plane by a first angle, the first and second surfaces converging from the proximal sidewall toward the distal sidewall, the spacer including an opening from the first surface to the second surface and extending to the proximal sidewall forming a gap in the proximal sidewall such that the gap permits bone growth between the two bone portions at the proximal opening of the osteotomy; and permitting bone to grow through the gap in the proximal side wall.

In another aspect of the invention, a method of correcting the angular alignment of a bone includes: creating an osteotomy in a bone in which the osteotomy partially divides the bone into two bone portions connected by a bony hinge, the osteotomy having a proximal opening in a medial cortical surface of the bone and a distal vertex adjacent the bony hinge near a lateral cortical surface; inserting a wedge implant into the osteotomy through the opening in the medial cortical surface; and inserting a fastener through the lateral cortical surface and into engagement with the implant.

BRIEF DESCRIPTION OF THE DRAWINGS

Various examples of the present invention will be discussed with reference to the appended drawings. These drawings depict only illustrative examples of the invention and are not to be considered limiting of its scope.

FIG. 2b is a perspective view of coordinate planes illustrating the relationship between the surfaces of the implant of FIG. 2a.

FIG. 3 is a top plan view of the implant of FIG. 2a.

FIG. 4 is a front elevation view of the implant of FIG. 2a.

FIG. 5 is a side elevation view of the implant of FIG. 2a.

FIG. 17 is a top plan view of the instrument of FIG. 16 showing an alternative arrangement for attaching the instrument to a bone.

FIG. 18 is a detail top plan view showing a modification to the instrument of FIG. 17.

FIG. 26 is a top plan view of a dilator according to the present invention.

FIG. 27 is an exploded perspective view of an insertion instrument and drill guide according to the present invention.

FIG. 28 is a cross sectional detail view showing the use of the insertion instrument of FIG. 27 with the implant of FIG. 2a.

FIG. 29 is a cross sectional detail view showing the use of the insertion instrument of FIG. 27 with the implant of FIG. 2a.

FIGS. 30-36 depict steps in using the instruments of FIGS. 16 and 27 with the implant of FIG. 2a.

DESCRIPTION OF THE ILLUSTRATIVE EXAMPLES

Figure 1:
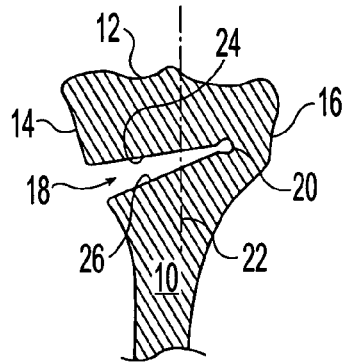
FIG. 1 is a front elevation view of a tibia showing an illustrative high tibial osteotomy.

Examples of an osteotomy system include a wedge implant and an osteotomy guide. The wedge implant may include a wedge-shaped spacer that is inserted into an osteotomy in a bone to provide primary support to the osteotomy in an expanded position. The wedge implant may include superior and inferior planar surfaces that are offset by a first angle in a first plane to provide an angular correction to the bone. The wedge implant may interface at least partially with the bone surfaces of the osteotomy.

Alternatively, the superior surface of the wedge implant may be offset from the inferior surface by two angles to provide a dual correction. The first angle is as described above whereas the second angle lies in a second plane. For example, in a tibial osteotomy, a change in the posterior tibial slope may be desired by the surgeon to restore the posterior tibial slope to an anatomically normal angle, to decrease the angle of posterior tibial slope for patients who have instability related to ACL deficiency, or for other surgical purposes.

Alternatively, the second angle may be provided to facilitate a less invasive surgical procedure in which the wedge implant is inserted into the osteotomy along a linear drive direction oblique to the osteotomy vertex. For example, in a tibial osteotomy, the wedge implant may be inserted approximately normal to the anterior medial tibial cortex at the location of the osteotomy. The first and second angles may be sized to compensate for this oblique insertion direction such that the two angles cooperate to provide a correction only in the coronal plane. The angles may also be sized to provide a dual correction such that the two angles cooperate to provide both a coronal alignment correction and a sagittal alignment correction when the wedge implant is inserted obliquely.

The wedge implant may be shaped to support the osteotomy by at least partially engaging the cancellous bone within the osteotomy. It may further engage the cortical bone surrounding the osteotomy such as at the anterior medial cortex and/or the posterior cortex in a tibial osteotomy. Cortical engagement can better resist bending moments resulting from compressive loading of the bone. The wedge implant may include a lip, or flange, to engage the cortical bone surface and act as a stop during insertion. This lip may extend onto the cortex, may conform to the cortical surface, and may function as a bone plate by featuring holes to receive bone screws through the cortex. Alternatively, the bone plate may be a separate piece. The bone plate may resist valgus loading, which would tend to open a medial tibial osteotomy, flexion-extension moments, rotational forces between the bone sections superior and inferior to the osteotomy, and extrusion of the wedge implant from the osteotomy. The bone plate may be made of a different material than the wedge implant.

The wedge implant may feature at least one cannulation that is aligned transversely to the vertex of the osteotomy in an axial view of the bone. The cannulation may receive a bone screw that is inserted through the wedge implant, for example from medial to lateral, to engage the cortex opposite the osteotomy opening to prevent the wedge implant from extruding from the osteotomy under loading. The cannulation may be directed such that it does not intersect the vertex of the osteotomy in order to prevent the bone screw from violating the remaining bone at the hinge point for the osteotomy. Alternatively, the wedge implant may be pulled into the osteotomy to expand and support it. The wedge implant may be pulled into place by one or more bone screws, or bolts, anchored to the opposite cortex. Screws may bear directly on the cortex or may abut a plate which bears on the cortex.

The wedge implant may have serrated superior and inferior surfaces to purchase into the bone surfaces within the osteotomy to prevent extrusion. The serrations alone may adequately prevent extrusion for smaller amounts of correction, which would subject the wedge implant to generally lower extrusion forces; however, larger amounts of correction may require additional fixation such as the plate or bone screw described above for proper stabilization.

The wedge implant may be shaped to provide at least one opening between opposite sides of the osteotomy to allow bone to grow across the osteotomy. The opening may be located adjacent to the osteotomy opening since bone growth at the osteotomy opening would provide the most mechanical leverage for resisting compressive and tensile loads across the osteotomy opening due to its relatively large distance from the osteotomy vertex. The opening in the spacer may also be shaped to accommodate a tibial tunnel for other procedures such as ACL or PCL reconstruction in a tibia with no or little removal of wedge implant material during the reconstruction drilling process. The wedge implant may also feature micro- or macro-pores to allow bone in-growth, or through-holes or channels oriented to allow cancellous bone growth across the osteotomy. The pores and/or channels may contain bone growth promoting substances. The wedge implant may also contain at least one channel oriented to allow injection or insertion of bone cement and/or bone growth promoting substances into the osteotomy after seating the implant.

The wedge implant may be made in a variety of sizes, corresponding to different amounts of angular correction determined by the surgeon to correct the misalignment. The wedge implant may be shaped such that it is symmetric. This would enable one range of wedge implant sizes to be used in both left and right cases, and would decrease the amount of inventory required by the manufacturer and the end user.

The wedge implant and/or the bone screws and/or the plate may be made of a non-resorbable or resorbable polymer, a metal, a ceramic, or a combination thereof. The material may further be solid, or have micro- or macro-pores, or have through holes or a combination thereof, for allowing in-growth of bone. The material may also contain bone growth promoting substances such as osteoconductive additives such as autograft bone, allograft bone, bone paste, demineralized bone matrix, beta tricalcium phosphate, hydroxyapatite, and/or other suitable osteoconductive additives and/or osteoinductive additives such as bone morphogenic proteins, growth factors, platelet rich plasma, and/or other suitable osteoinductive additives. The material may also contain voids or pockets to allow injection of a bone cement to provide fixation after implantation and/or the pockets may be filled with bone growth promoting substances. The pockets may be in the form of a semi-uniform "honeycomb" or cellular shape to maximize or improve the structural compressive properties of the wedge.

The instrumentation system for preparing the bone to accept the wedge implant may include a guide with medial and lateral arms that are temporarily and rigidly clamped onto the bone. The medial and lateral arms may each feature a prong to purchase onto the cortex; the prongs may be cannulated to receive a pin to further secure the guide after positioning. The guide may be used to reference the medial and lateral cortices for sawing, drilling and advancing screws. The arms of the guide may be screw driven to allow for adjustment of guide width and application of a clamping force between the two arms using a manual or powered driver. Alternatively, the arms may be manually sliding and allow locking for positioning. At least one of the arms may accommodate or may be formed by one of several modular attachments, which may include a cutting/sawing guide, a dilator and osteotomy sizer, a temporary implant, drill guides, and an inserter for the implant. The wedge implant may be pushed into the tibial cut to expand the osteotomy using the guide.

The guide may feature a drill guide to allow for the placement of a drill hole at the vertex of the osteotomy. A vertex hole would decrease the stress concentration at the vertex of the osteotomy during dilation, thereby decreasing the likelihood of propagation of stress fractures across the bone at the hinge point or into the tibial plateau. The hole may be positioned and drilled prior to creation of the osteotomy to aid orienting the vertex relative to the coronal plane. Furthermore, the hole may be located at a predetermined distance relative to one of the guide arms to ensure that the proper amount of bone is left as a hinge for the osteotomy. The drill may be left in place after creation of the hole to provide an anchor point to stabilize the guide on the bone. The drill may also be left in place to serve as a positive guard to prevent sawing past the desired osteotomy vertex. The guide may be symmetric about a mid-plane to allow use in both left and right cases.

The guide may be secured onto the bone using temporary percutaneous screws/pins. For placement, the guide may have alignment marks or attachments to indicate its location and angle relative to one or more anatomical landmarks such as the tibial plateau, long bone axis, or other suitable landmark prior to securing the guide onto the bone.

The guide may include a swivel arm which is fixable in two planes and which carries the vertex drill guide and the saw guide, thereby constraining the vertex to lie within the sawing plane. The swivel arm would provide movement in two axes should the surgeon require it to correctly orient the vertex drill. Once the desired orientation is found, the arm is fixed in place by means of a knob or other suitable method. In a modular guide, the modular attachments may attach to the swivel arm.

The figures depict illustrative examples of an osteotomy system. The examples will be described in terms of an opening high tibial osteotomy directed generally from medial to lateral. However, the examples are illustrative only and should not be considered as limiting the scope of the invention. The osteotomy system of the present invention may be used at other locations and from other directions to perform an opening osteotomy.

Referring to FIG. 1, a tibia 10 includes a tibial plateau 12, a medial side 14, a lateral side 16, and a tibial osteotomy 18. The tibial osteotomy 18 in this example was made by making a single cut from the medial side 14 of the tibia toward the lateral side 16 ending at a vertex 20. The osteotomy 18 is then opened angularly about the vertex 20 to obtain a desired alignment of the tibial plateau 12 relative to the tibial axis 22. The opened osteotomy 18 has opposing side walls 24 and 26.

Figure 2A:
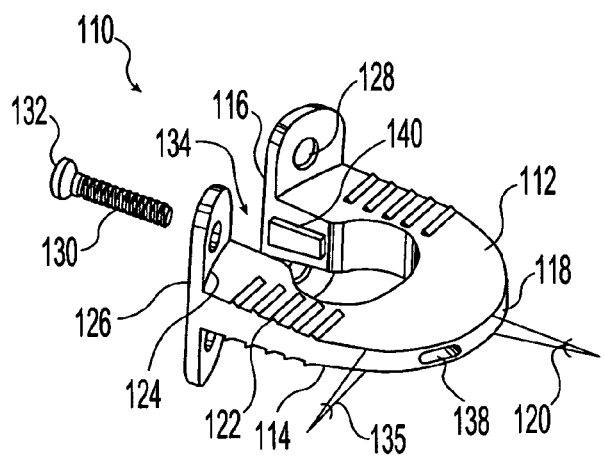
FIG. 2a is a perspective view of an illustrative wedge implant according to the present invention.
Figure 3:
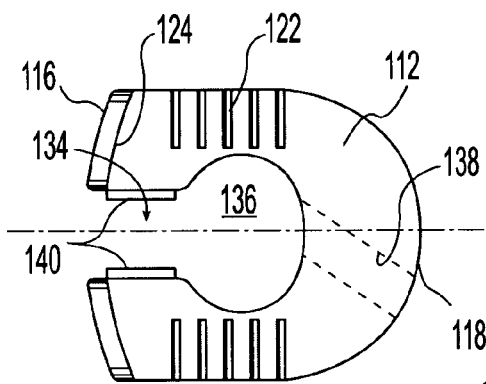
Figure 2B:
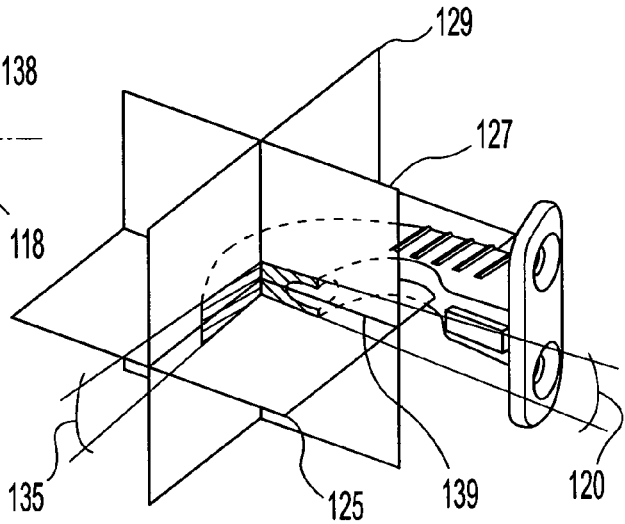
Figure 4:
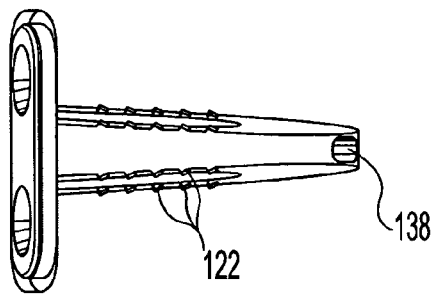
Figure 5:
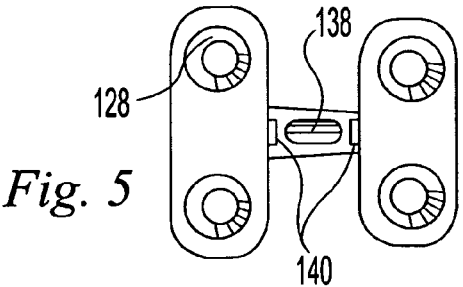

Referring to FIGS. 2a-5, an illustrative wedge implant 110 includes a body having a superior planar surface 112, an inferior planar surface 114, a proximal end 116, and a distal end 118. The superior and inferior surfaces 112, 114 are angled relative to one another and diverge from the distal end 118 toward the proximal end 116 to form a wedge. The angle between the superior and inferior surfaces 112, 114 may be described in terms of component angles alpha 120 and beta 135 projected into a coordinate system as illustrated in FIGS. 2a, 2b, and 3. The wedge implant 110 has an insertion axis 139 FIG. 2b) corresponding to the direction of insertion of the wedge implant 110 into the osteotomy 18. A first coordinate plane, or midplane, 125 corresponds to a plane through the wedge implant 110 spaced evenly between the superior and inferior surfaces 112, 114 such that it bisects the angle between the surfaces 112, 114. A second coordinate plane, or insertion axis plane, 127 contains the insertion axis 139 and is normal to the midplane 125. A third coordinate plane 129 is normal to both the midplane 125 and the insertion axis plane 127. The angle alpha 120 is the angle between the superior and inferior surfaces 112, 114 in the insertion axis plane 127. The angle beta 135 is the angle between the superior and inferior surfaces 112, 114 in the third coordinate plane 129 normal to the insertion axis plane. The angular correction of the tibial alignment may be described in terms of these two component angles 120, 135. For example, if angle beta 135 is zero, the angle between the surfaces 112, 114 will lie in the insertion plane 127. If beta 135 is not zero, the angle between the surfaces 112, 114 will lie between the insertion axis plane 127 and the third plane 129 normal to the insertion axis plane 127.

The wedge implant 110 is inserted into the osteotomy 18 with the distal end 118 leading such that the superior and inferior planar surfaces 112, 114 engage the sides 24, 26 of the osteotomy 18 and provide primary internal support to maintain the osteotomy 18 in the open position. The wedge implant 110 may be driven into the osteotomy 18 to cause the osteotomy 18 to open or it may be placed after the osteotomy 18 has been opened by another means such as with a dilator instrument. Teeth 122 projecting from the superior and inferior planar surfaces 112, 114 engage the sides 24, 26 of the osteotomy 18 to prevent extrusion of the wedge implant 110. A lip 124 extends above and/or below the superior and inferior surfaces 112, 114 to provide an insertion stop. Upon full insertion, the lip 124 will bottom on the cortical surface of the bone adjacent the osteotomy 18 opening to arrest the forward motion of the wedge implant 110. In the illustrative example of FIGS. 2a-5, the lip 124 extends both superiorly and inferiorly to form a fixation plate 126 having counterbored through holes 128 for receiving bone screws 130. The bone screw heads 132 abut the plate 126 and the screws 130 thread into the bone adjacent to the osteotomy 18. The plate 126 and screws 130 resist extrusion of the wedge implant 110, opening of the osteotomy 18 in the superior-inferior direction, flexion-extension moments, and rotational forces on the osteotomy. In a medial osteotomy, the plate 126 and screws 130 resist medial extrusion of the wedge implant 110 and valgus loads that would tend to bend open the medial opening of the osteotomy 18.

In the illustrative wedge implant 110, the component angles alpha and beta 120, 135 are designed to accomplish various surgical goals depending on the surgical approach taken. In one example, a medial high tibial osteotomy 18 is directed from a medial opening toward a lateral vertex 20. If the angle beta 135 is zero such that the angle between the superior and inferior surfaces 112, 114 lies within the insertion axis plane 127 and the wedge implant 110 is inserted straight into the osteotomy 18 within the coronal plane, the osteotomy 18 will be opened and supported at the angle alpha 120 in the coronal plane. However, it may be desirable to also change the tibial plateau 12 alignment in another direction. For example, it may be desirable to change the posterior slope of the tibial plateau in the sagittal plane. This is provided for in the illustrative wedge implant 110, by making the angle beta 135 nonzero such that the angle between the superior and inferior surfaces 112, 114 lies between the insertion plane 127 and the third plane 129 such that insertion of the wedge implant in the coronal plane will result in both coronal plane and sagittal plane corrections.

In another example, it is desirable to insert the wedge implant 110 obliquely such as from the anterior medial direction to minimize the incision required and/or to avoid disrupting the medial collateral ligaments. If only the angle alpha 120 is non-zero and the wedge implant 110 is inserted obliquely, the tibial plateau 12 alignment will be changed in both the coronal plane and the sagittal plane. By utilizing the second angle beta 135, the degree of change in alignment in the coronal and sagittal planes can be independently controlled. For example, if it is desired to have only a change in alignment in the coronal plane, the angles may be sized to nullify the out-of-plane effects of an oblique insertion. Alternatively, the angles may be sized to create both a predetermined coronal plane correction and a predetermined sagittal plane correction.

The illustrative wedge implant 110 includes a proximal gap 134 extending from the superior surface 112 to the inferior surface 114 near the proximal end 116 of the implant 110 to permit bone growth between the opposite sides of the osteotomy. Bone growth at the proximal opening of the osteotomy 18 supports the osteotomy 18 and is positioned furthest from the osteotomy vertex 20 to best resist opening forces. The illustrative wedge implant 110 further includes a central opening 136 extending from the superior surface 112 to the inferior surface 114 and communicating with the proximal gap 134. The central opening 136 likewise permits bone growth for long term support of the osteotomy. The central opening 136 also provides an opening for the passage of other implants such as an anterior cruciate ligament replacement. Both the proximal gap 134 and the central opening 136 further serve to reduce the volume of implant material that is introduced into the osteotomy and provide space for the insertion of bone growth promoting substances.

In the illustrative wedge implant 110 of FIGS. 2-5, a portal 138 extends distally through the implant 110 from the central opening 136 to the distal end 118 to permit bone growth promoting substances to be inserted through the implant 110 into the distal region of the osteotomy 18 near the vertex 20. The illustrative portal 138 is angled relative to the insertion axis 139 such as to direct the portal perpendicularly into the vertex 20 when the wedge implant 110 has been inserted obliquely.

The illustrative wedge implant 110 further includes a pair of lugs 140 projecting into the proximal gap 134 for engaging an insertion instrument so that the wedge implant 110 may be oriented and inserted in the direction of the insertion axis 139.

The wedge implant 110 may be made of metal, plastic, ceramic, glass, bone, and/or other suitable materials. For example, the wedge implant 110 may include metals including stainless steels, titanium, titanium alloys, cobalt-chromium steels, nickel-titanium alloys, and/or other suitable metals. The wedge implant 110 may include nonresorbable polymers including polyolefins, polyesters, polyimides, polyamides, polyacrylates, poly(ketones), fluoropolymers, siloxane based polymers, and/or other suitable nonresorbable polymers. The wedge implant 110 may include resorbable polymers including polyesters (e.g. lactide and glycolide), polyanhydrides, poly(aminoacid) polymers (e.g. tyrosine based polymers), and/or other suitable resorbable polymers. The wedge implant 110 may include other materials including nonresorbable and resorbable ceramics (e.g. hydroxyapitite, calcium sulfate) or biocompatible glasses. The wedge implant 110 may include bone growth promoting substances such as osteoconductive additives such as autograft bone, allograft bone, bone paste, demineralized bone matrix, beta tricalcium phosphate, hydroxyapatite, and/or other suitable osteoconductive additives and/or osteoinductive additives such as bone morphogenic proteins, growth factors, platelet rich plasma, and/or other suitable osteoinductive additives. These additives may be included in any suitable amounts. They are preferably included at a rate of from 20% to 80% by weight. The wedge implant 110 may include a homogenous material structure and/or composite structures. Different portions of the wedge implant 110 may be made of different materials to impart different properties to the different portions. For example, the fixation plate 126 may be made of a malleable material to permit it to deform or be shaped to the contour of the cortical bone against which it abuts. The wedge implant 110 body may be made of a rigid material capable of providing primary support to the osteotomy 18 during the healing period. The elastic modulus of the wedge implant 110 body may be approximately equal to the elastic modulus of the surrounding bone to minimize stress shielding of the bone. Stress shielding is the phenomenon in which healing of bone adjacent to the implant is impaired due to the implant having a much higher modulus than the bone and thus shielding the bone from exposure to physiologic loads, which are necessary to induce healing. As a specific example, the wedge implant 110 body may be made of homogenous resorbable poly-L-lactic acid (PLLA) polymer and the fixation plate 126 may be made of PLLA polymer in which the polymer chains have been oriented by drawing in one or more directions to align the chains and impart directional strength and malleability. The fixation plate 126 may be molded onto the wedge implant 110 body, pinned on, solvent welded to, or otherwise joined to the wedge implant 110 body.

Figure 6:
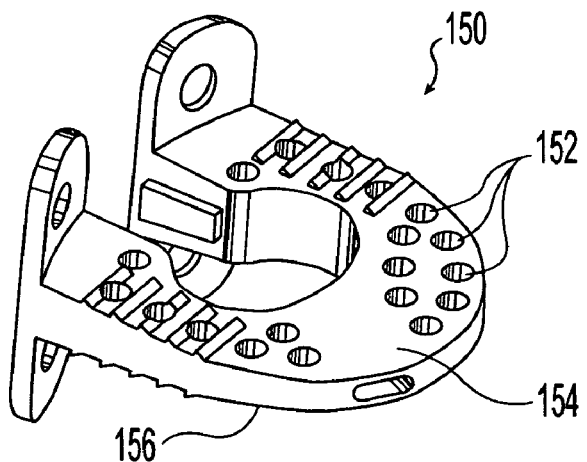
FIG. 6 is a perspective view of the implant of FIG. 2a showing an alternative arrangement of bone growth promoting holes.
Figure 7:
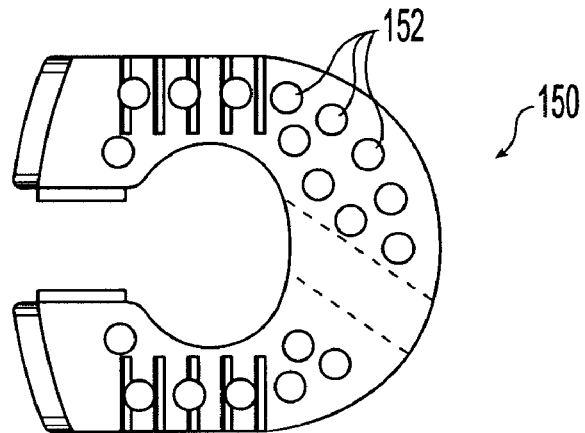
FIG. 7 is a top plan view of the implant of FIG. 6.
Figure 8:
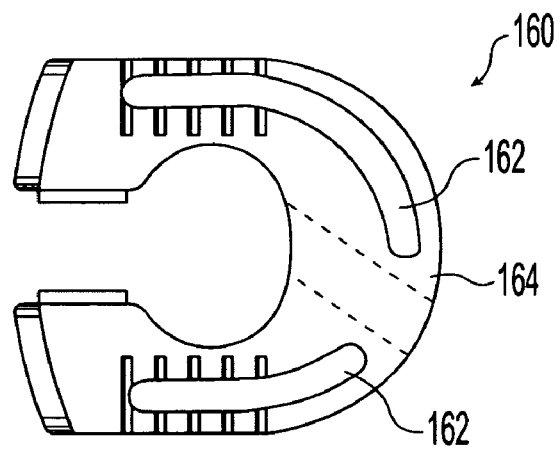
FIG. 8 is a top plan view of the implant of FIG. 2a showing an alternative arrangement of bone growth promoting holes.

FIGS. 6 and 7 depict a modification of the wedge implant 110 of FIGS. 2-5. The modified wedge implant 150 includes a plurality of vertical through holes 152 that extend from the superior surface 154 to the inferior surface 156 to facilitate bone growth through the body of the wedge implant 150. FIG. 8 shows a similar modification in which a wedge implant 160 includes vertical through channels 162 or elongated holes that extend from the superior surface 164 to the inferior surface and along a path approximately parallel to the outer profile of the wedge implant 160 to facilitate bone growth through it. The holes 152 of FIGS. 6-7 and the channels 162 of FIG. 8 may be left open or be filled with bone growth promoting substances prior to insertion of the wedge implant 160.

Figure 9:
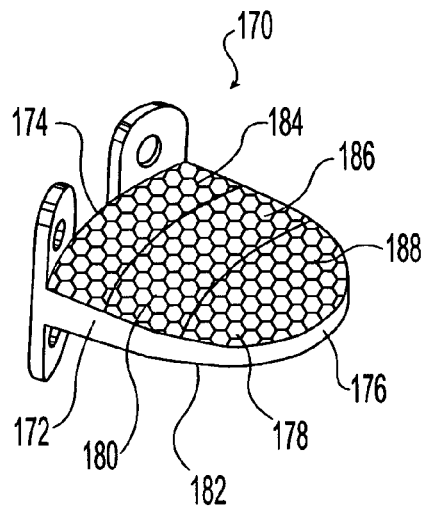
FIG. 9 is a top plan view of the implant of FIG. 2a showing an alternative arrangement of bone growth promoting holes.

FIG. 9 depicts a modification to the wedge implant 110 of FIGS. 2-5. The modified wedge implant 170 includes an implant body 172 tapering from a proximal end 174 to a distal end 176. The implant body 172 includes a porous structure in which the pores 178 extend from the superior surface 180 to the inferior surface 182. The implant body 172 may be made from a resorbable material and the pores 178 may be filled with one or more resorbable materials. For example the body 172 may be made of a resorbable polymer such as PLLA polymer. The pores 178 may be filled with a resorbable ceramic that will impart compression strength to the implant 170 sufficient to support the osteotomy 18. In this example, the polymer acts as a container to retain the ceramic. The wedge implant 170 will resorb while bone is growing across the osteotomy. The ceramic filler in the pores 178 supports the bone growth. Eventually, the wedge implant 170 will be substantially resorbed and replaced by bone. The pores 178 can be selectively filled with a gradient of resorbable materials to tailor the osteoconductivity and support provided to the osteotomy. For example, the implant body 172 may be divided into multiple zones 184, 186, 188 arranged radially from proximal to distal. Since the osteotomy 18 is narrower distally, bone can bridge the distal portion of the osteotomy more quickly than it can proximally. Also, since the loads on the implant are less at the distal end 176, the support requirements are less. Thus, a relatively rapidly resorbing filler may be placed in the distal zone 188 where bone will grow across quickly while the more proximal zones 184, 186 continue to support the osteotomy. For example, the distal zone 188 may be filled with a relatively rapidly resorbing ceramic such as calcium sulfate, the intermediate zone 186 may be filled with a less rapidly resorbing ceramic such as beta tricalcium phosphate, and the proximal zone 184 may be filled with a less rapidly resorbing ceramic such as hydroxy apatite. The resorption rates can be further tailored by using combinations of these materials or other suitable materials in the zones.

The pore structure of the implant body can be produced in any suitable way. For example, large pores such as the illustrated hexagonal honeycomb structure may be molded or machined directly into the implant. Alternatively, smaller pores may be used such as can be produced by foaming the polymer. In this case, the pores may only extend partway into the implant body.

Figure 10:
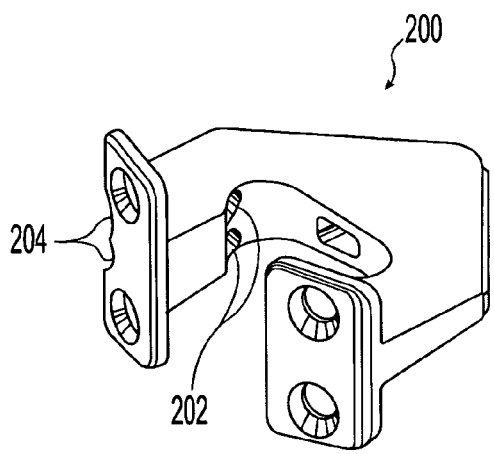
FIG. 10 is a perspective view of the implant of FIG. 2a showing an alternative arrangement of fixation holes for securing the implant to a bone.
Figure 11:
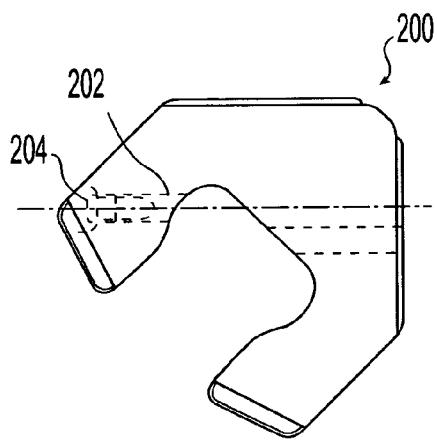
FIG. 11 is a top plan view of the implant of FIG. 10.
Figure 12:
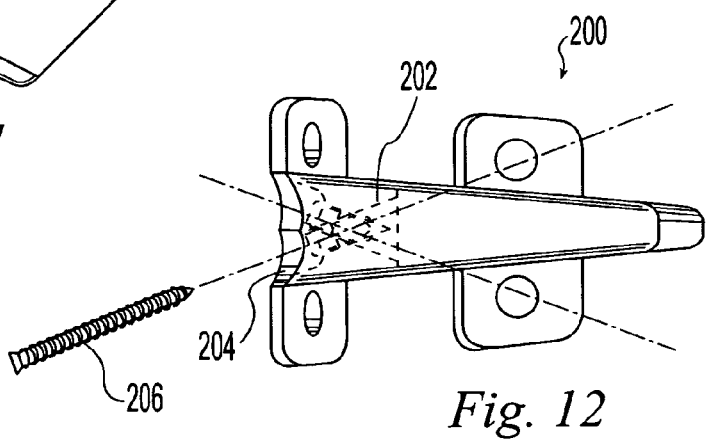
FIG. 12 is a side elevation view of the implant of FIG. 10.

FIGS. 10-12 depict a modification of the wedge implant 110 of FIGS. 2-5. The modified wedge implant 200 includes at least one cannulation 202 that is aligned transversely to the vertex 20 of the osteotomy 18 as shown in the axial view of the tibia in FIG. 11. The cannulation 202 may include a counterbore 204 to receive a bone screw 206 that is inserted through the wedge implant 200 from medial to lateral to engage the lateral cortex. In the illustrative wedge implant 200 of FIGS. 10-12, a pair of cannulations is provided to accommodate a screw 206 angled upwardly or one angled downwardly. The cannulations 202 may be directed superiorly and inferiorly as seen in FIG. 12 such that they do not intersect the vertex 20 of the osteotomy 18. This alignment prevents the bone screw 206 from violating the remaining bone at the vertex 20 forming the hinge point for the osteotomy 18.

Figure 13:
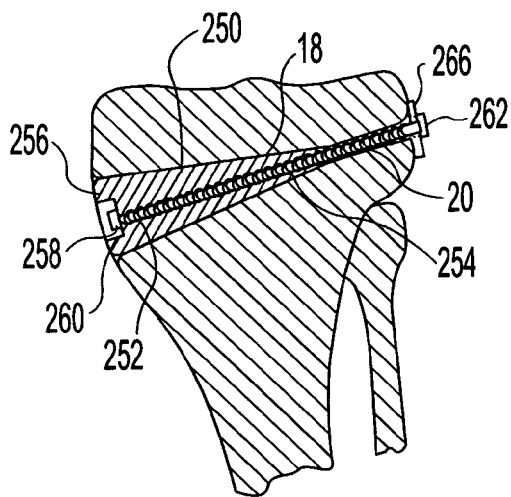
FIG. 13 is a side elevation view of the implant of FIG. 2a showing an alternative arrangement of fixation holes for securing the implant to a bone.
Figure 14:
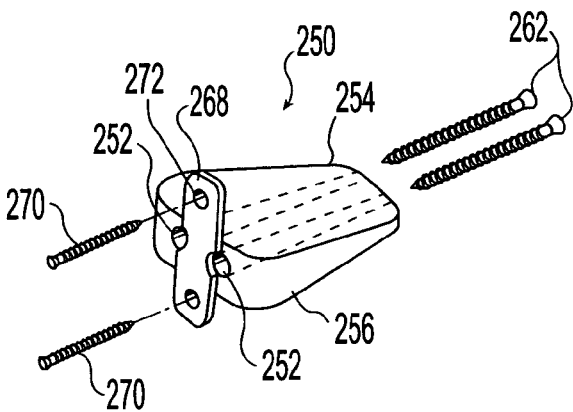
FIG. 14 is a perspective view of the implant of FIG. 13 showing a fixation plate in use with the implant.

FIGS. 13-14 depict a modification of the wedge implant 110 of FIGS. 2-5. The modified wedge implant 250 includes at least one longitudinal bore 252 from the distal end 254 to the proximal end 256 of the implant 250. The bore 252 may be threaded or a separate nut 258 may be provided in a counterbore 260 to receive a screw 262 from the opposite cortex 264. In the illustrative example of FIGS. 13-14, two bores 252 are provided for two screws 262 directed from the lateral cortex toward the wedge implant 250. In this example, the wedge implant 250 is pulled into and/or held in the osteotomy by tightening the screws 262. The longitudinal bore 252 may be axial as shown or it may be angled superiorly or inferiorly to avoid the vertex 20 of the osteotomy 18. An optional washer 266 is shown in FIG. 13 to better distribute the screw forces on the cortex 264. A fixation plate 268 having transverse holes 272 and an additional pair of screws 270 may optionally be used to resist opening of the osteotomy and provide additional resistance to extrusion of the wedge implant 250.

Figure 15:
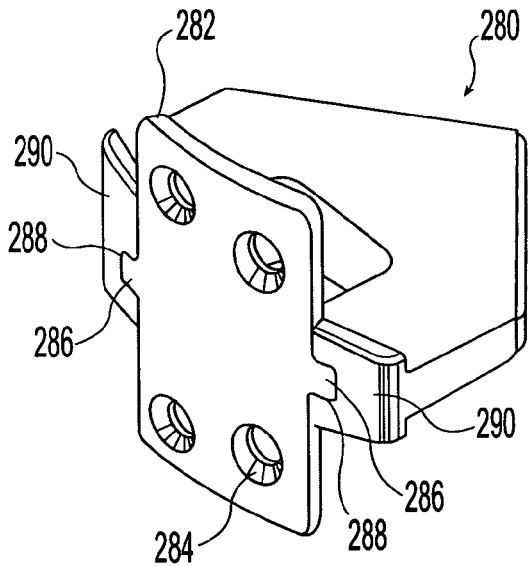
FIG. 15 is a perspective view of the implant of FIG. 2a showing an alternative arrangement for a fixation plate for securing the implant to a bone.

FIG. 15 depicts a modification of the wedge implant 110 of FIGS. 2-5. The modified wedge implant 280 includes a modular fixation plate 282. The plate 282 includes counterbored holes 284 for receiving bone screws that insert into the bone adjacent to the osteotomy opening. The plate 282 further includes a pair of tabs 286 that seat in corresponding notches 288 in the proximal side 290 of the wedge implant 280. The tab-to-notch engagement may be a sliding fit, a press fit, a snap fit, or other suitable engagement. The plate 282 may be assembled to the wedge implant 280 before or after insertion of the wedge implant 280 into the osteotomy. The tab-to-notch engagement aids in centering the plate 282 over the osteotomy opening to provide the same amount of bone superiorly and inferiorly for the bone screws to engage.

Figure 16:
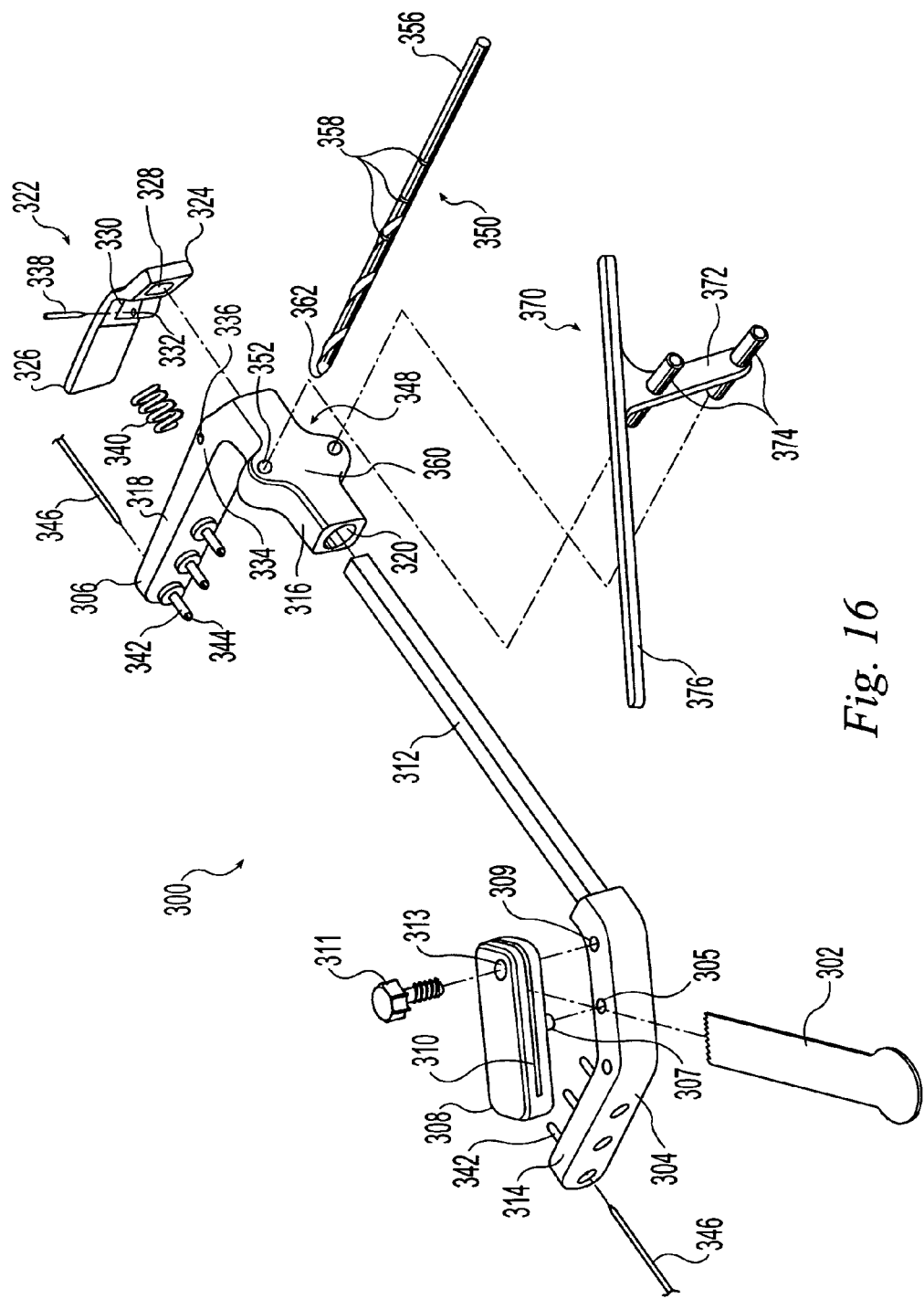
FIG. 16 is an exploded perspective view of an instrument for performing an osteotomy according to the present invention.
Figure 19:
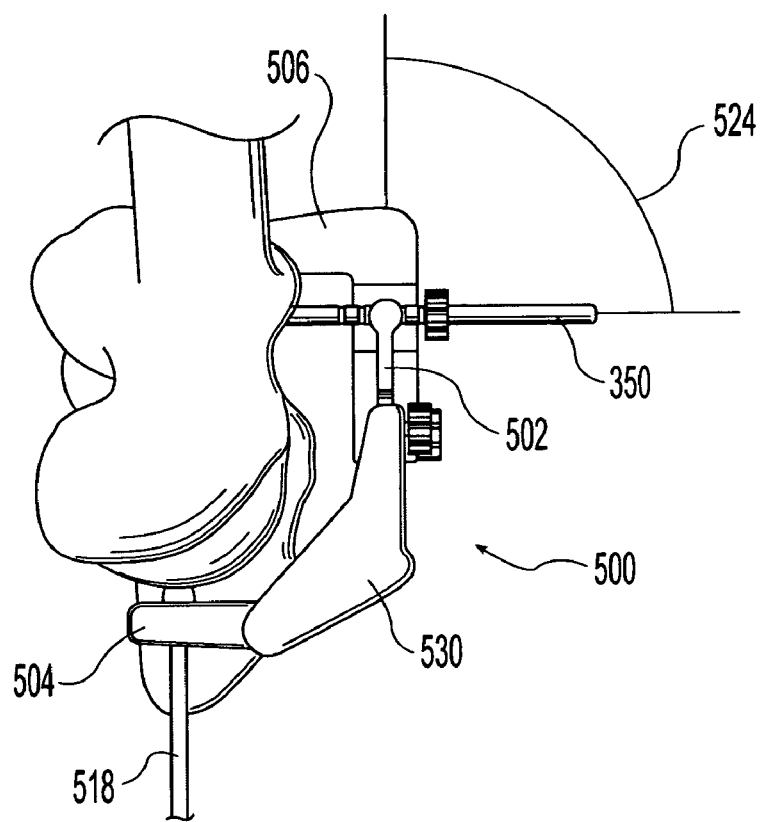
FIG. 19 is a perspective view of the instrument of FIG. 16 shown attached to a bone and showing an alternative adjustment mechanism.
Figure 20:
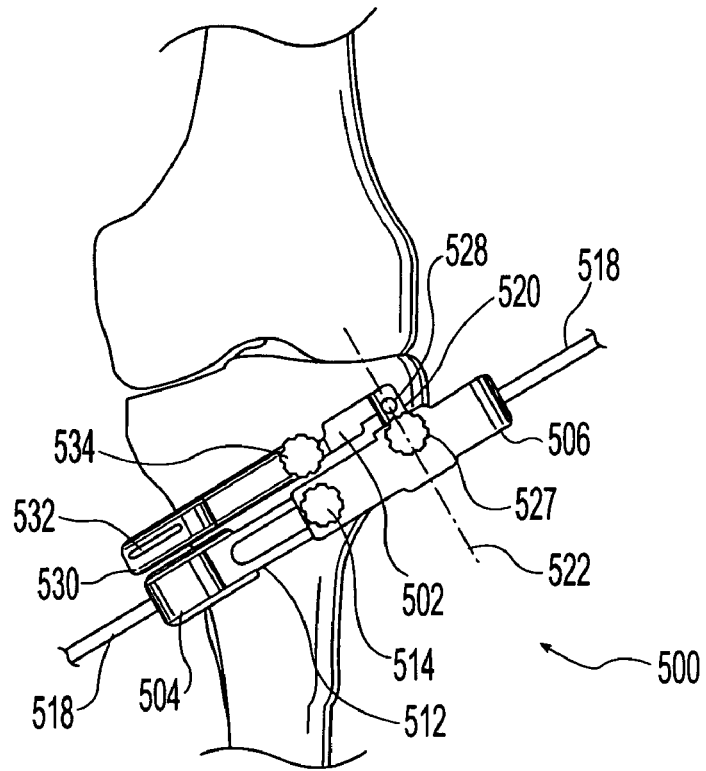
FIG. 20 is a front elevation view of the instrument of FIG. 19.
Figure 21:
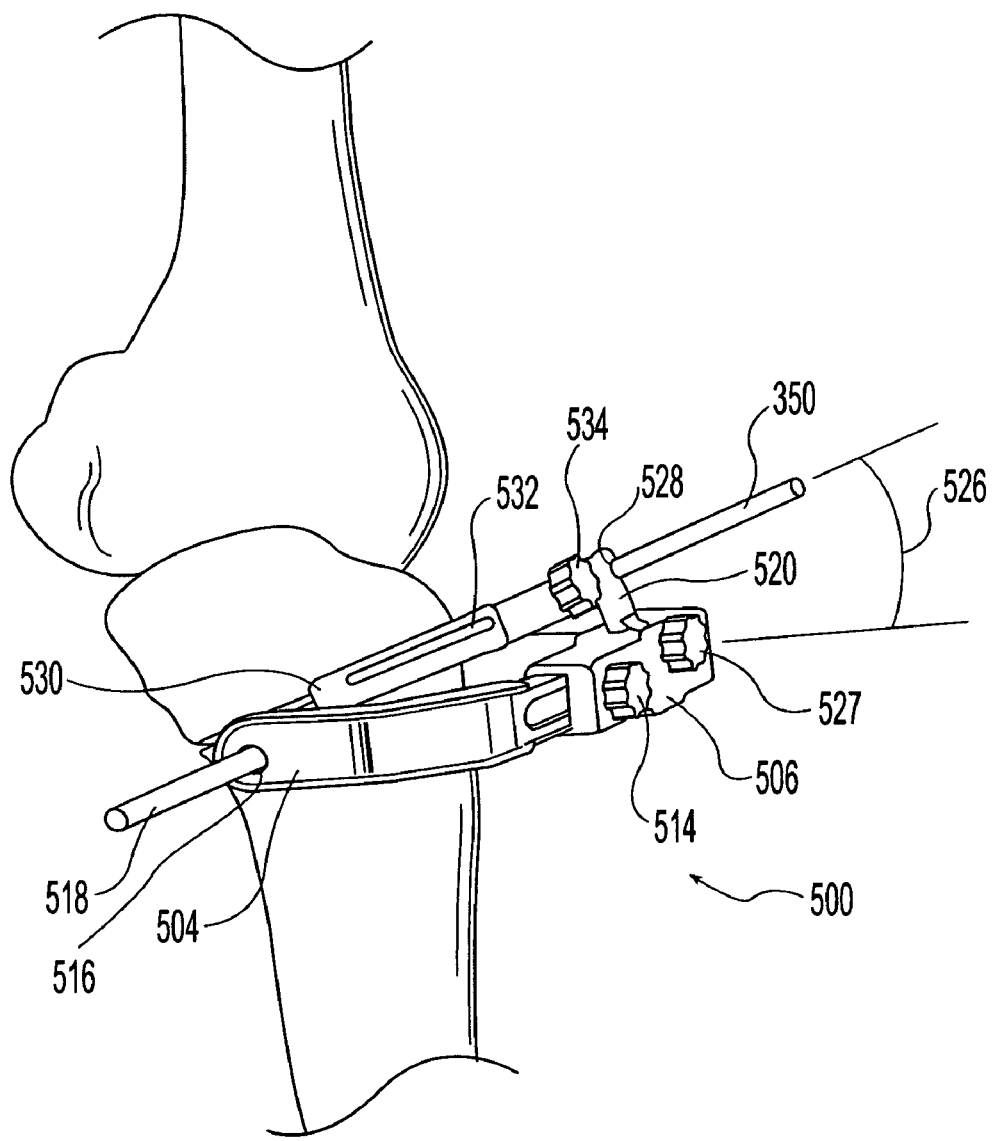
FIG. 21 is a perspective view of the instrument of FIG. 19.

FIG. 16 depicts an illustrative osteotomy guide 300 for guiding a saw blade 302 in cutting the osteotomy 18. The guide 300 includes medial and lateral arms 304, 306 that clamp the bone and support a saw guide 308 having a slot 310 for receiving the saw blade 302 and guiding it at the desired osteotomy location. The medial arm 304 includes a shaft 312 and a head 314 mounted on the shaft 312 and angled transversely to the shaft 312. The lateral arm 306 includes a body 316 and a head 318 mounted on the body 316 and angled transversely to the body 316. The body includes a longitudinal through bore 320 for slidingly receiving the shaft 312 of the medial arm 304. In the illustrative example of FIG. 16, the heads 314, 318 of the medial and lateral arms 304, 306 are oriented perpendicular to the medial arm shaft 312 and lateral arm body 316 so that they are parallel to one another and are compressible to abut the medial and lateral sides of the bone to accommodate a variety of bone sizes.

A locking lever 322 includes a shaft engaging end 324 and an actuator end 326. The shaft engaging end 324 includes an opening 328 for receiving the shaft 312 of the medial arm 304. The locking lever 322 includes a fulcrum 330 projecting outwardly and including a pivot hole 332. The fulcrum 330 is received by the lateral arm 306 in a saddle 334 in pivoting relationship. The saddle includes a pivot hole 336 aligned with the pivot hole 332 of the locking lever 322. A pin 338 is pressed into the pivot holes 332, 336 to retain the locking lever 322 on the lateral arm 306. A spring 340 is positioned between the actuator end 326 and the lateral arm 306 to bias the actuator end 326 outwardly away from the lateral arm 306 and consequently to bias the shaft engaging end 324 toward the lateral arm 306. When the actuator end 326 is depressed toward the lateral arm 306, the shaft opening 328 aligns with the longitudinal through bore 320 and permits the shaft 312 of the medial arm 304 to slide in the longitudinal bore 320 and the shaft opening 328. When the actuator end 326 is released, the shaft opening 328 binds against the shaft 312 of the medial arm 304 locking it in place. Thus, the locking lever 322 may be actuated to permit sliding adjustment of the spacing of the medial and lateral arms 304, 306 and released to lock them relative to one another.

The medial and lateral arms 304, 306 include prongs 342 for insertion through skin incisions and for abutting cortical bone. The prongs 342 include longitudinal bores 344 for receiving elongated pins 346 to affix the guide 300 to the bone. Multiple prongs 342 are provided at varying radial distances from the shaft 312 to accommodate different sizes of bones. In the illustrative example of FIG. 16, three prongs 342 are provided on each arm to provide three different radial distances. The saw guide 308 is offset superiorly or inferiorly from the prongs so that the path of the saw blade 302 will not intersect the fixation pins 346. The saw guide 308 may be formed as an integral part of the medial arm 304 or as a separate component. In the illustrative example of FIG. 16, the saw guide is a provided as a separate component releasably mountable on opposite superior and inferior sides of the medial arm 304. In this way, the guide 300 can be flipped over for use on both left and right tibias and the saw guide 308 remounted to give a consistent offset. The medial arm includes a first mounting hole 305 that receives an alignment pin 307 projecting from the saw guide 308 and a second, threaded, mounting hole 309 that receives a bolt 311 passed through a bore 313 in the saw guide 308. When the bolt 311 is tightened the saw guide is secured in a predetermined alignment relative to the guide 300.

The guide 300 includes a drill guide 348 for guiding a drill 350 to form a hole defining the vertex 20 of the osteotomy 18. In the illustrative example of FIG. 16, the drill guide 348 is formed as an integral part of the lateral arm 306 and is located at a predetermined longitudinal distance from the prongs 342 of the lateral arm 306 such that it will guide the drill 350 to form a vertex hole a predetermined distance from the lateral cortex. This distance determines the width of the lateral hinge of the osteotomy 18. It has been found that a hinge width between 1 and 2 centimeters is suitable. Alternatively, the drill guide 348 may be mounted so that the longitudinal distance from the prongs 342 of the lateral arm 306 is adjustable to allow for adjustable hinge widths. The drill guide 348 includes a drill guide bore 352 that receives and guides the drill 350. In the illustrative guide 300, a pair of drill guide bores 352 is provided. Each of the drill guide bores 352 corresponds to the plane of the saw blade slot 310 when the saw guide 308 is mounted in one of its alternate locations.

The drill 350 includes index marks 358 spaced along its shaft 356. Each index mark 358 is positioned to align with the front surface 360 of the drill guide 348 when the tip 362 of the drill 350 is extended to a depth equal to one of the opposing pairs of prongs 342. By visualizing the alignment of the prongs 342 with the bone and the relative position of the index marks 358 relative to the front surface 360 of the drill guide 348, the user can determine the approximate position of the drill tip 362 relative to the bone.

An alignment rod 370 may be provided to aid in aligning the guide 300 on the bone. The alignment rod includes a base 372 including a pair of mounting pins 374 projecting outwardly from the base 372 and a boom 376. The mounting pins 374 are insertable into the drill guide bores 352 to position the boom 376 at a fixed angle relative to the saw guide slot 310. The boom 376 can then be used to position the saw guide slot 310 at the fixed angle relative to an anatomic feature. For example, in the illustrative example of FIG. 16, the boom 376 is at an angle of 30 degrees relative to the slot 310. By placing the boom 376 parallel to the tibial plateau 12, the saw guide slot 310 will be positioned at an angle of 30 degrees relative to the tibial plateau 12. An angle of 30 degrees has been found to position the osteotomy 18 on the bone in a position that reduces the risk of fracturing the bone and that provides sufficient room for fixation screws superior and inferior to the osteotomy 18.

FIG. 17 depicts a modification of the guide 300 of FIG. 16. In the modified guide 400, the three pairs of opposing prongs 342 of FIG. 16 have been replaced by a single pair of opposing adjustable prongs 402. The prongs 402 are mounted for sliding in opposing radial slots (not shown) formed in each of the medial and lateral arms 404, 406. Each arm 404, 406 includes a transverse slot 408 intersecting the radial slots. Each prong 402 includes a head 410, a threaded shaft 412, and a lock nut 414. Each prong 402 is mounted in one of the opposing radial slots such that it extends through the slot and opposes the other prong 402. The prongs 402 may be adjusted radially inwardly and outwardly by sliding them in the radial slots. The lateral prong may also be made to be axially adjustable to allow for adjusting the distance from the prong to the vertex drill guide. This would permit adjustment of the osteotomy hinge width.

The head 410 of each prong 402 abuts the outside surface 405 of the arm 404, 406 to prevent the prong 402 from passing inwardly through the radial slot. A lock nut 414 is threaded onto the shaft 412 of each prong 402 and rides in the transverse slot 408. The lock nut 414 abuts the inside surface 416 of the transverse slot 408 to prevent the prong from passing outwardly through the radial slot. The lock nut 414 can be tightened so that the head 410 and lock nut 414 press tightly against the outside and inside surfaces 405, 416 respectively of the arms 404, 406 and slots 408 to lock the prongs 402 at a desired radial position relative to the shaft 420 of the guide 400. The prongs 402 may be adjusted to accommodate varying thicknesses of soft tissue in the area where the prongs contact the bone.

Since the prongs are separately slidable, they may be differentially adjusted to change the inversion/eversion angle (angle about the long axis of the bone) of the guide 400. This allows for the placement of the vertex drill 350 to be fine-tuned after the guide 400 is placed and pinned. For example, it may be used to adjust the drill guide 400 so that the vertex 20 is directed to lie within the sagittal plane. In order to allow this adjustment, the pins 346 may be made out of a bendable material such as nitinol and/or the prongs may have an additional degree of freedom of rotation within the plane of the guide. For example, an alternative prong 422 is shown in FIG. 18. The prong 422 includes a shaft 424 having a transverse through hole 426. A cylindrical pivot pin 428 is mounted in the hole 426 and rides in the transverse slot 408. The head 430 threads onto the shaft 424 and includes a spherical back surface 425 for engaging the outside surface 405 of the arm. The prong is permitted to swivel about the axis of the pin 428 to permit fine tuning of the inversion/eversion angle. Tightening the head 430 against the outside surface 405 of the arm locks the prong 422 in place radially and angularly.

FIGS. 19-22 depict a modification of the guide 300 of FIG. 16. The modified guide 500 includes a swivel arm 502 which provides an alternative means of adjusting the vertex drill 350 angle and the sawing plane for the osteotomy 18. The guide includes medial and lateral arms 504, 506. The medial arm 504 includes a shaft 512 mounted in sliding relationship to the lateral arm 506. A locking knob 514 may be loosened to permit sliding adjustment of the spacing of the medial and lateral arms 504, 506 and tightened to lock them relative to one another. The medial and lateral arms 504, 506 include holes 516 for receiving pins 518 to attach the guide 500 to the bone.

The swivel arm 502 is mounted on the guide 500 with two degrees of freedom. In the illustrative example of FIGS. 19-22, the swivel arm 502 includes a shaft 520 having a shaft axis 522. The shaft 520 is mounted on the lateral arm 506 for rotation of the swivel arm 502 about the shaft axis 522. This rotation adjusts a first angle 524 affecting the direction of the vertex drill similar to the concept of inverting/everting the guide using slidable and swiveling prongs as described relative to FIG. 18. The shaft 520 is also mounted for rotation, or hinging, in and out of the plane parallel to the view of FIG. 20, thus affecting a second angle 526 of the vertex drill 350 and sawing plane similar to the concept of pivoting the guide 300 about the pins 346 as described relative to FIG. 16. A locking screw 527 is tightened to lock the swivel arm 502 in place.

The guide 500 includes a drill guide for guiding the drill 350 to form the hole defining the vertex 20 of the osteotomy 18. In the illustrative example of FIGS. 19-22, the drill guide is formed as an integral part of the swivel arm 502 and includes a bore 528 through the swivel arm to receive the drill 350. The guide 500 also includes a saw guide 530 having a slot 532 for receiving the saw blade 302 and guiding it at the desired osteotomy location. In the illustrative example of FIGS. 19-22, the saw guide is a modular member mounted on the swivel arm and locked in place by a locking screw 534.

Figure 23:
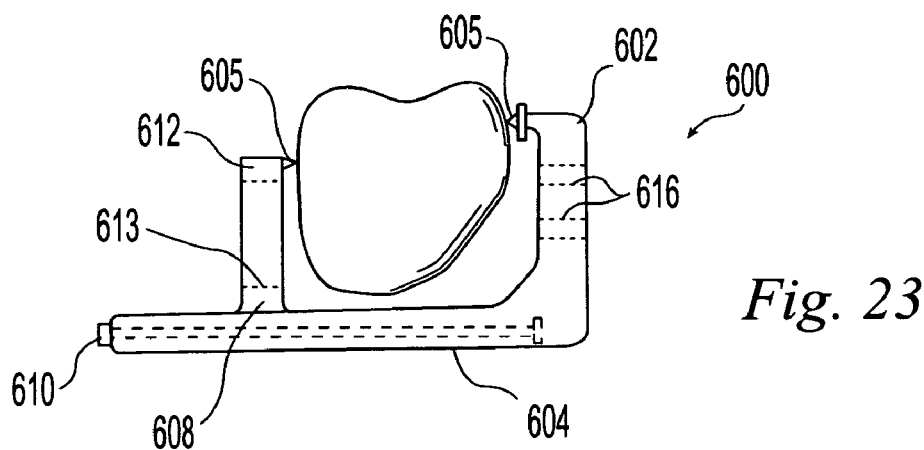
FIG. 23 is a top plan view of the instrument of FIG. 16 showing an alternative modular component mounting.
Figure 24:
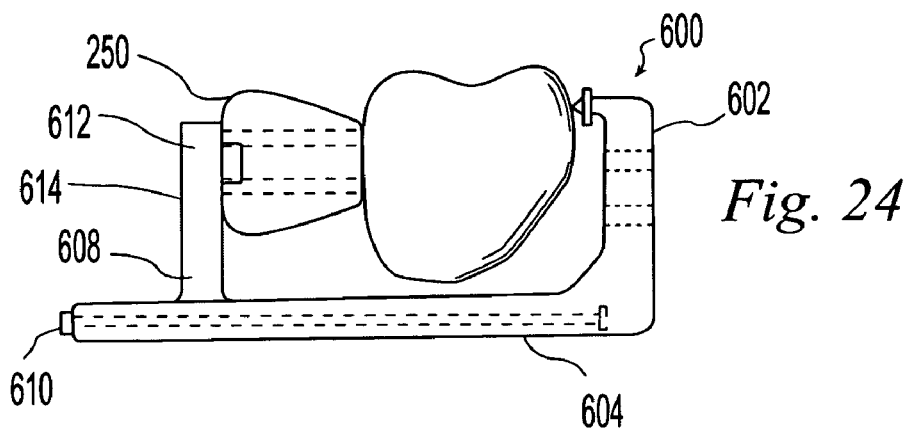
FIG. 24 is a top plan view of the instrument of FIG. 23 showing another alternative modular component mounting.

FIGS. 23 and 24 depict a modification of the guide 300 of FIG. 16. In the modified guide 600, the lateral arm 602 includes an elongated rail 604 extending medially. A medial arm 608 is mounted for sliding on the rail 604. A screw 610 threads through the medial arm 608 and is mounted to the lateral arm 602 so that it can rotate but not translate. Rotation of the screw 610 causes the medial arm 608 to translate along the rail 604 toward or away from the lateral arm 602 such that a clamping force may be applied between the two arms 602, 608 by rotating the screw 610 with a manual or powered driver. The arms 602, 608 include inwardly directed fixation spikes 605 that grip the bone. The medial arm 608 may include a plurality of modular attachments, which may include a clamping arm 612, a cutting/sawing guide 613 like the saw guide 308 of FIG. 16, a dilator/osteotomy sizer, a temporary implant, drill guides, and an inserter for the implant 614. The implant inserter 614 is shown in FIG. 24 attached to the implant 250 of FIGS. 13 and 14. Turning the screw 610 will cause the inserter 614 to drive the implant 250 into the osteotomy. A dilator/osteotomy sizer may be shaped like the implant 250 and driven into and then retracted from the osteotomy as in FIG. 24 to open the osteotomy before insertion of the implant 250 if desired. Different sizes of dilator/sizers may be inserted sequentially until the desired correction is achieved. An implant may then be selected based on the size of dilator that resulted in the desired correction. A temporary implant may be provided that is similar to the dilator/sizer but that may be disengaged and left in the osteotomy temporarily while the guide 600 is removed in order to check joint kinematics or otherwise assess the sufficiency of the correction. A drill guide may be attached to the medial arm to guide a drill in forming holes in the bone aligned with the holes 128 of the implant 110 of FIGS. 2-5, the holes 204 of the implant 200 of FIGS. 10-12, the holes 252 or 272 of the implant 250 of FIGS. 13 and 14, or the holes 284 of the implant 280 of FIG. 15. Alternatively, the holes may be formed from the lateral side by a drill guided by drill guide holes 616 formed in the lateral arm 602.

Figure 22:
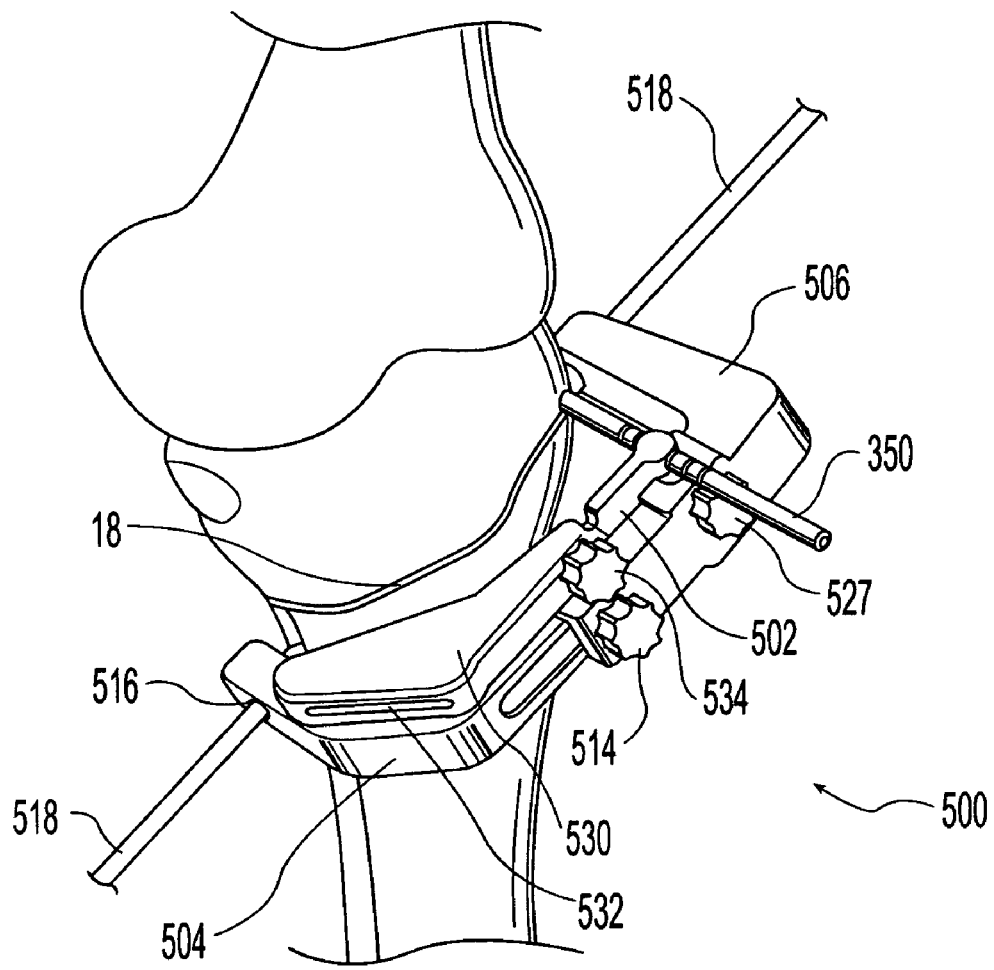
FIG. 22 is another perspective view of the instrument of FIG. 19.
Figure 25:
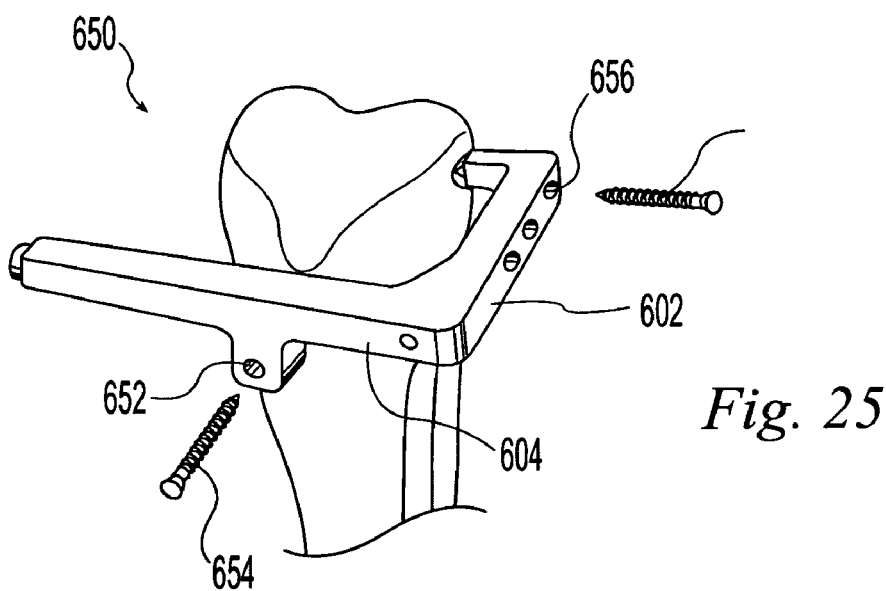
FIG. 25 is a perspective view of the instrument of FIG. 23 showing an alternative means of attaching the instrument to a bone.

FIG. 25 depicts a modification to the guide 600 of FIGS. 22 and 23. The modified guide 650 includes an anterior bore 652 through the rail 604 to receive an anterior fixation screw 654 to fix the angle of the guide 650 in the sagittal plane. The guide 650 further includes a lateral bore 656 through the lateral arm 602 to receive a lateral fixation screw 658 to fix the angle of the guide 650 in the coronal plane.

FIG. 26 depicts a dilator 700 that may be used to dilate the osteotomy prior to inserting the wedge implant 110. Alternatively, the dilator 700 may be omitted and the wedge implant 110 may be inserted so that it dilates the osteotomy upon insertion. The dilator includes a head 702 having the same basic wedge shape as the wedge implant 110. A handle 704 is attached to the head 702 to facilitate insertion of the head 702 into the osteotomy 18. The head 702 may be inserted by manual pressure on the handle 704 or by impacting the handle 704. A plurality of different sizes of dilators 700 may be inserted sequentially to progressively open the osteotomy 18 or a single dilator 700 may be inserted to fully open the osteotomy 18 in one step.

FIGS. 27-29 depict an implant inserter 720 for use with the implant 110 of FIGS. 2-5. The inserter 720 includes a shaft 722 having a proximal end 724 and a distal end 726. The proximal end 724 is mounted to a handle 728. The distal end 726 includes opposing notches 725 (one shown) for engaging the lugs 140 of the implant 110. The lugs 140 extend into the notches to constrain the orientation of the wedge implant 110 relative to the inserter 720 along the insertion axis 139 (FIG. 3). The lugs 140 bottom against a shoulder 727 at the proximal end of the notches 725 to permit an axial insertion force to be imparted from the inserter 720 to the wedge implant 110 along the insertion axis 139. An axial bore 730 extends through the handle 728 and through the shaft 722 from the proximal end 724 to the distal end 726. The notches 725 are sized so that the distal end of the driver shaft 722 seats adjacent to the portal 138 in the implant 110 with the axial bore 730 directed into the portal 138. A side loading port 732 communicates from the outside of the shaft 722 to the axial bore 730 to permit material to be inserted through the port 732 and into the axial bore 730. A plunger 734 includes a solid shaft 736 and a knob 738 mounted on the proximal end 740 of the shaft 736. The distal end 742 of the shaft 736 is sized for sliding engagement with the axial bore 730 such that the plunger 734 and axial bore 730 form a syringe-like arrangement. When the plunger 734 is fully inserted into the axial bore 730, the distal end 742 of the plunger shaft 736 extends distally past the side loading port 732 and closes the port 732. In the illustrative embodiment, the distal end 742 of the plunger shaft 736 extends to the distal end 726 of the inserter shaft 722. By pulling the knob 738, the plunger 734 may be retracted so that the distal end 742 of the plunger shaft 736 is moved proximal to the port 732 to open the port 732. Material may then be inserted through the port 732 into the axial bore 730. Pressing the knob 738 to slide the plunger 734 distally will expel the material from the distal end 726 of the inserter shaft 722 and into the portal 138 of the wedge implant 110.

A drill sleeve 750 may be provided for guiding a drill to form holes in the cortical bone aligned with the counterbored through holes 128 of the wedge implant 110. The drill sleeve 750 includes a drill tube 752 sized to receive the drill and a handle 754 mounted to the drill tube 752 to facilitate positioning the drill sleeve 750. The distal end 756 of the drill tube 752 seats in the counterbored holes 128 to guide the drill. An optional drill sleeve guide 760 may be provided to constrain the direction of the drill sleeve 750. The drill sleeve guide 760 includes a body 762 having a slot 764 for engaging the inserter shaft 722. The slot 764 may include inwardly directed lugs or pins (not shown) to engage the notches 725 in the inserter shaft 722. Each lug bottoms against the shoulder 727 at the proximal end of the notches 725. The wedge implant 110 is then assembled onto the inserter 720 and bottoms on the drill sleeve guide 760. The drill sleeve guide 760 may be removably mountable on the shaft 722 or it may be permanently mounted. Elongated tabs 766 extend superiorly and inferiorly away from the body 762. The tabs 766 include elongated through holes 768 whose long axes are in the superior-inferior direction. In use, the wedge implant 110 is mounted on the inserter 720 and the drill sleeve 750 is passed through the drill sleeve guide 760 to engage the counterbored through holes 128 in the wedge implant 110.

FIGS. 28-29 show the alignment of the drill sleeve 750, relative to the drill sleeve guide 760 and implant holes 128. FIG. 29 depicts the case where the fixation plate 126 is not bent. With the drill tube 752 abutting the top 770 of the elongated hole 768, the drill tube 752 will direct a drill normal to the plate 126 so that a fixation screw can be seated normal to the plate 126. The gap 772 between the bottom of the elongated hole 768 and the drill tube 752 would permit the drill tube 752 to be angled upwardly to direct the drill at an angle away from the wedge implant 110 and osteotomy 18. However, the proximity of the top 770 of the elongated hole 768 prevents drill tube 752 from being angled downwardly past the normal so that the drill tube 752 cannot direct the drill into the wedge implant 110 or osteotomy 18. This arrangement protects the wedge implant 110 and osteotomy hinge. FIG. 28 depicts the case where the fixation plate 126 is bent outwardly to accommodate an outwardly sloping cortical bone. The gap 772 between the bottom of the elongated hole 768 and the drill tube 752 permits the drill tube 752 to be angled upwardly to direct the drill at an angle away from the wedge implant 110 and osteotomy 18 to form a hole normal to the plate 126 so that a fixation screw can be seated normal to the plate 126.

Figure 30:
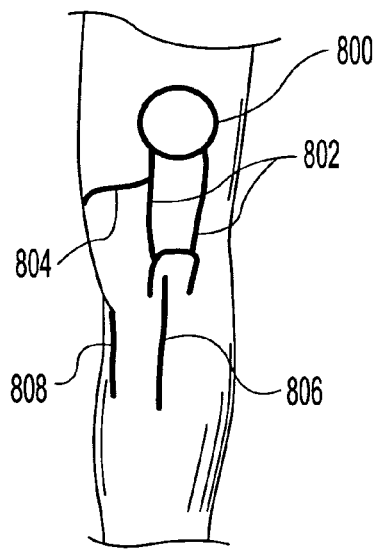

FIGS. 30-36 depict a minimally invasive surgical technique using the implants and instruments of the present invention to perform a medial opening wedge high tibial osteotomy. The surgical approach is through the anterior-medial tibial cortex to avoid the medial collateral ligament. FIG. 30 shows a knee joint with anatomical landmarks marked on the skin to aid the surgeon in placing the guide 300 on the tibia. The landmarks are palpated and the patella 800 is outlined as is the patellar tendon 802. A line is drawn at the level of the medial tibial plateau 804. A line is drawn corresponding to the anterior-medial edge 806 of the tibia and another line is drawn corresponding to the posterior medial edge 808 of the tibia.

Figure 31:
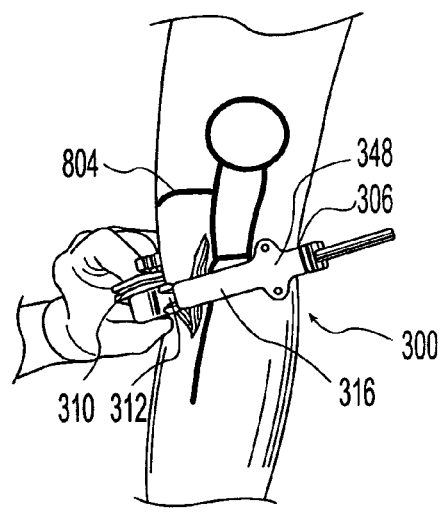
Figure 32:
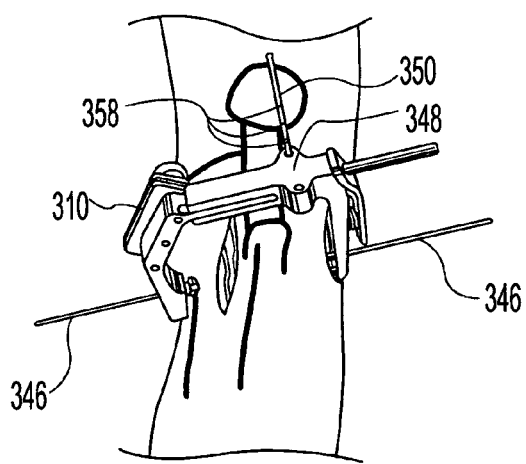
Figure 33:
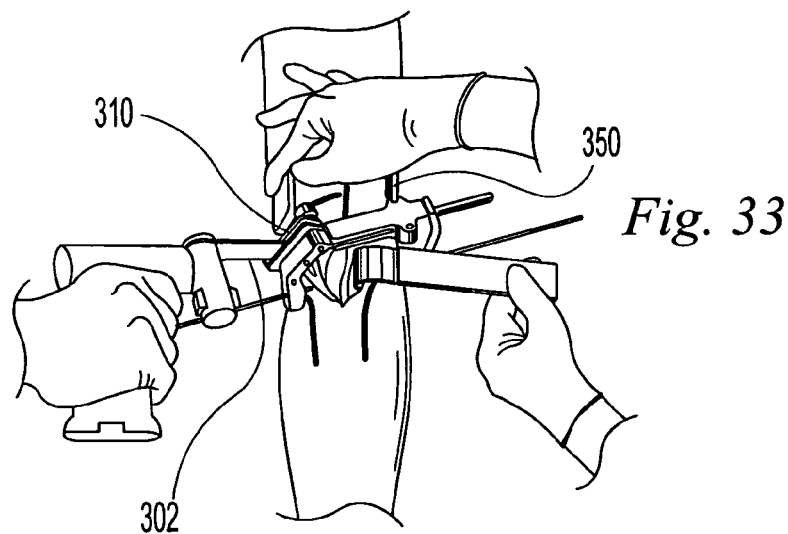
Figure 34:
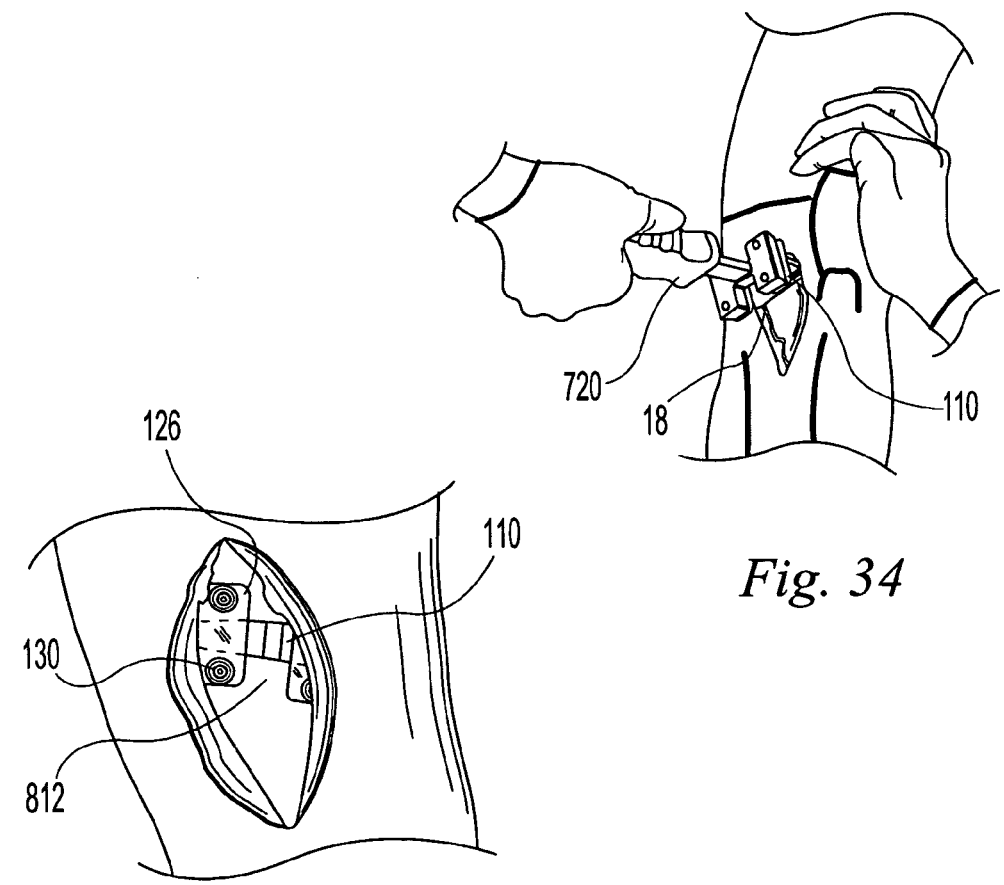
Figure 35:
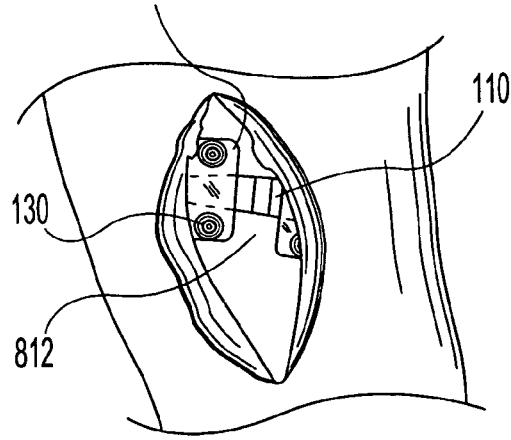
Figure 36:
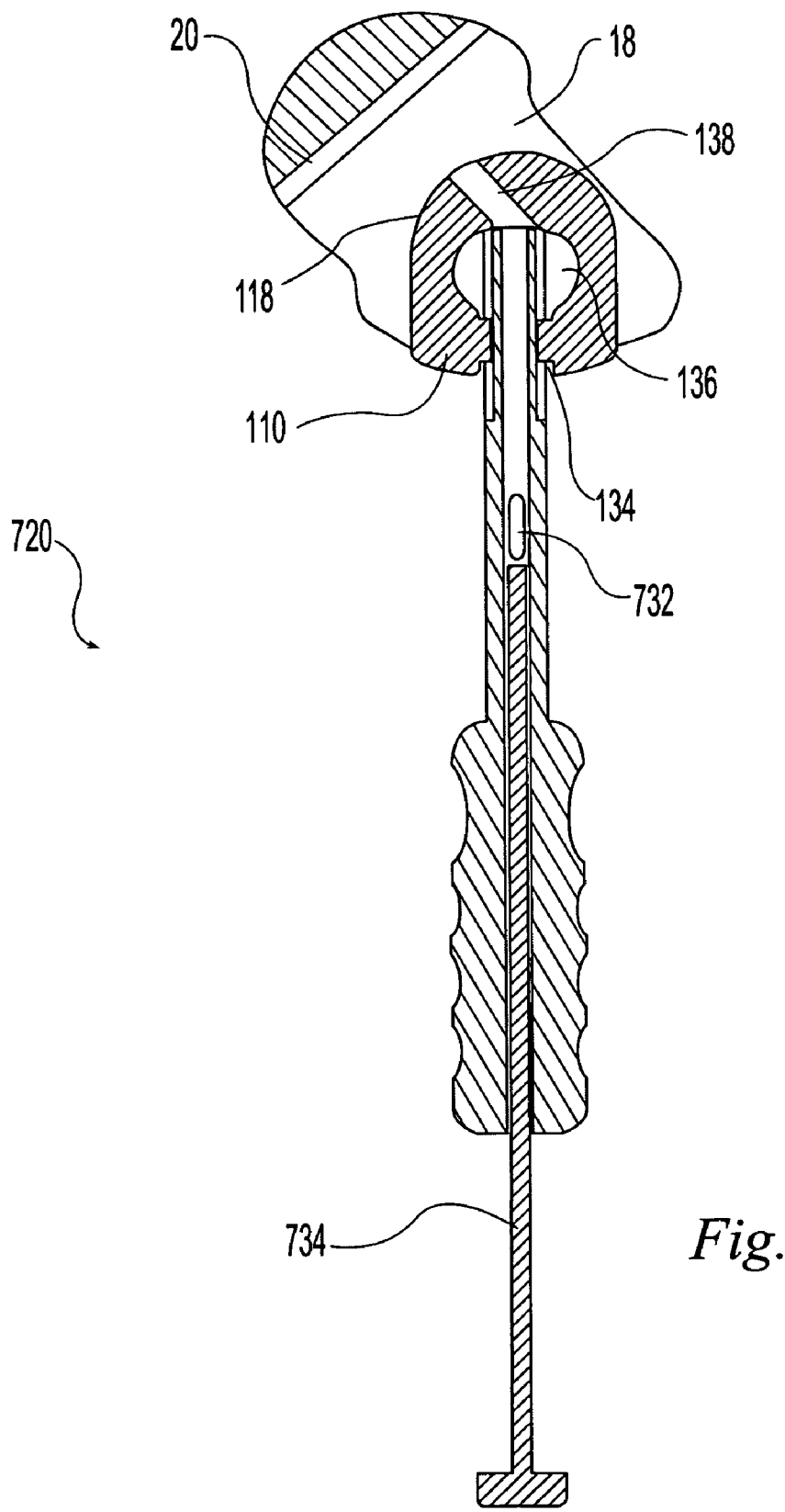

Referring to FIG. 31, one of the lateral prongs of the guide 300 is placed through a stab incision to abut the lateral tibial cortex approximately 1.5 cm distal to the lateral tibial plateau. After the guide is angled 30 degrees, this will result in the vertex 20 of the osteotomy 18 being approximately 1.5 cm below the plateau. The corresponding medial prong is placed through a stab incision to abut the medial tibial cortex with the saw blade slot 310 angled approximately 30 degrees to the tibial plateau 804. The angle can be approximated by visualizing the medial arm shaft 312 and lateral arm body 316 at a 30 degree angle. Alternatively, alignment rod 370 (FIG. 16) may be mounted to the vertex drill guide 348 and the boom 376 positioned parallel to the tibial plateau 804 to establish the angle. Once the angle is set, pins 346 are driven through the prongs and into cortical bone as shown in FIG. 32. The guide 300 can now be pivoted about the pins 346 to establish the desired angle of the vertex drill in the sagittal plane. A drill 350 may be positioned in the vertex drill guide 348 and used to visualize the angle of the drill relative to the posterior slope of the tibia in the sagittal plane. In the illustrative technique, the guide angle is set to guide the drill 350 parallel to the posterior slope. The drill 350 is advanced to form an anterior-posterior hole that will define the vertex of the osteotomy and to pin the guide 300 to the bone at the desired sawing angle. The drilled hole acts to relieve the stresses at the vertex of the osteotomy. The index marks 358 on the drill 350 can be referenced and compared to the prong 342 positions to determine the approximate posterior location of the drill tip 362. The drill 350 is left in place to shield the saw blade 302 from over penetrating beyond the desired vertex 20 of the osteotomy 18. As shown in FIG. 33, the saw blade 302 is advanced through the slot 310 in the saw guide 308 and swept anteriorly and posteriorly to form the osteotomy 18. The blade 302 is advanced up to the drill 350 and withdrawn. Alternatively, the blade 302 may be used to create a cut of partial depth and the osteotomy 18 may be complete by impacting an osteotome along the cut up to the drill 350. The drill 350 and guide 300 are now removed from the bone. A dilator 700 may optionally be inserted to open the osteotomy. The dilator may also be used to determine the appropriate implant size. Dilators with different thicknesses and different alpha and beta angles 120, 135 may be inserted until the desired correction is obtained. As shown in FIG. 34, the appropriate implant 110 is attached to the inserter 720 and driven into the osteotomy 18. The fixation plates 126 may bend upon insertion to conform to the anterior-medial cortex 812 if necessary. Alternatively, the fixation plates 126 may be pre-bent prior to insertion if necessary. The drill sleeve 750 and drill sleeve guide 760 may be used to drill through the fixation plates 126 and into the anterior-medial tibial cortex to prepare screw holes. Bone screws 130 are driven to secure the wedge implant 110 as shown in FIG. 35. As shown in FIG. 36, the inserter 720 may be used to inject bone growth promoting substances into the osteotomy 18 between the distal end of the wedge implant 110 and the vertex 20 of the osteotomy by using the plunger 734 to expel the material through the portal 138 in the distal end of the wedge implant 110. After that portion of the osteotomy is filled, the inserter 720 is withdrawn and the central opening 136 and proximal gap 134 are manually packed. Alternatively, the osteotomy 18 may be manually packed prior to and after insertion of the wedge implant 110 and the use of the plunger 734 omitted.

Although embodiments of an osteotomy system and its use have been described and illustrated in detail, it is to be understood that the same is intended by way of illustration and example only and is not to be taken by way of limitation. The osteotomy system may be used to form an osteotomy in a variety of locations for a variety of purposes. Two illustrative locations are in the upper tibia to perform an opening high tibial osteotomy and in the distal femur to perform an opening distal femoral osteotomy. The system can be adapted to perform an osteotomy on various aspects of a bone including medial, lateral, and other aspects. Additional variation and modifications to the illustrative osteotomy system and its use will be apparent to those of ordinary skill in the art, and the following claims are intended to cover all such modifications and equivalents.

What is claimed is:

1. A wedge-shaped spacer for insertion into a cooperating osteotomy formed in a bone, the osteotomy partially dividing the bone into two bone portions connected by a bony hinge, the osteotomy having a proximal opening at a cortical surface of the bone and a distal vertex adjacent to the bony hinge, whereby after said osteotomy is formed said proximal opening is forced apart such that said two bone portions pivot with respect to one another about said vertex, the wedge-shaped spacer comprising:
   a body having a first generally planar surface,
   a second generally planar surface,
   a proximal sidewall,
   a distal sidewall, and
   an insertion axis extending longitudinally from the distal sidewall to the proximal sidewall, the first and second surfaces being spaced further apart at a position adjacent to the proximal sidewall than at a position adjacent to the distal sidewall, such that a first non-zero angle is formed between said first and second surfaces in a first plane containing the insertion axis, the first and second surfaces being angled relative to one another in a second plane perpendicular to the insertion axis by a second angle, whereby insertion of the spacer into the osteotomy ensures that the two bone portions will be retained in desired relative positions controlled by said first and second angles; and
   at least one fixation plate extending generally orthogonally to one or both of the first and second surfaces,
   wherein said at least one fixation plate and said body are a unitary construction,
   wherein said at least one fixation plate is made of a material having properties differing from a material constituting portions of said body, said fixation plate material being relatively more malleable than said material constituting portions of said body, and
   wherein said body further defines an opening extending between the first surface and the second surface and forming a gap in the proximal sidewall, said gap extending approximately half the distance from the proximal sidewall to the distal sidewall, such that said spacer is generally U-shaped, whereby bone can grow between the two bone portions at the proximal side of the osteotomy.

2. The spacer of claim 1 wherein each fixation plate includes at least one transverse hole configured to receive a bone screw.

3. The spacer of claim 1 wherein said spacer is intended for insertion into an osteotomy formed in a tibia, and wherein the first and second angles are sized to produce a predetermined varus-valgus angular correction and a predetermined posterior slope angular correction.

4. The spacer of claim 1 wherein spacer comprises a bioresorbable material.

5. The spacer of claim 1, comprising a bore being formed in the body, the bore being at least partially threaded and extending through a portion of the body from near the distal end to near the proximal end and lying between the first and second surfaces over at least a portion of the length of the bore, the spacer further comprising a threaded fastener inserted into the bore and engaging the spacer such that one end of the fastener may be mounted on the bone and threaded into the bore in the spacer to translate the spacer toward the distal vertex.

6. The spacer of claim 1, wherein the spacer body comprises a plurality of zones comprising one or more bioresorbable materials, the zones having different rates of bioresorption.

7. The spacer of claim 6 wherein the rate of bioresorption of the zones is higher for zones nearer the distal end and lower for zones nearer the proximal end of the spacer.

8. The spacer of claim 6 wherein the spacer body comprises a porous structure in which the pores are filled with one or more resorbable materials.

9. The spacer of claim 8 wherein the body comprises a porous resorbable polymer and the pores in different zones are filled with different resorbable ceramics.

10. The spacer of claim 9 wherein the resorbable polymer comprises PLLA polymer and the spacer body comprises at least three zones arranged proximally to distally, the ceramics filling the pores comprising hydroxy apatite, beta tricalcium phosphate, and calcium sulfate proximally to distally.

11. The spacer of claim 1, comprising a bore being formed in the body, the bore to extend through a portion of the body from near the distal end to near the proximal end and lying between the first and second surfaces over at least a portion of the length of the opening, the bore extending longitudinally or transversely from the proximal end.

12. A wedge-shaped spacer for insertion into a cooperating osteotomy formed in a bone, the osteotomy partially dividing the bone into two bone portions connected by a bony hinge, the osteotomy having a proximal opening at a cortical surface of the bone and a distal vertex adjacent the bony hinge, whereby after said osteotomy is formed said proximal opening is forced apart such that said two bone portions pivot with respect to one another about said vertex, the wedge-shaped spacer comprising a body having first and second surfaces and proximal and distal sidewalls, the first and second surfaces being angled relative to one another, such that the first and second surfaces converge from the proximal sidewall toward the distal sidewall, the spacer including an opening extending between the first surface and the second surface to form a gap in the proximal sidewall, said gap extending approximately half the distance from the proximal sidewall to the distal sidewall, such that said spacer is generally U-shaped, whereby bone can grow between the two bone portions at a proximal side of the osteotomy, the spacer further comprising at least one fixation plate extending generally orthogonally to one or both of the first and second surfaces, said at least one fixation plate and said body being a unitary construction, said at least one fixation plate being made of a material having properties differing from a material constituting portions of said body, and said fixation plate material being relatively more malleable than said material constituting other portions of said body.

13. The spacer of claim 12 further comprising a plurality of openings formed between the first surface and the second surface to permit bone growth through the body of the spacer.

14. The spacer of claim 12 further comprising at least one elongated opening extending from the first surface to the second surface through said body, and along a path generally parallel to an outer profile of the spacer to permit bone growth through the body of the spacer.

15. The spacer of claim 12 wherein the opening is filled with a bone growth promoting substance.

16. The spacer of claim 12 wherein the spacer body is formed from a first resorbable polymer and the fixation plate is formed from a second resorbable polymer.

17. The spacer of claim 12 wherein the spacer body comprises a homogenous PLLA polymer and the fixation plate comprises a PLLA polymer in which the polymer chains have been oriented by drawing in one or more directions to align the chains and improve malleability.

18. A wedge-shaped spacer for insertion into a cooperating osteotomy formed in a bone, the osteotomy partially dividing the bone into two bone portions connected by a bony hinge, the osteotomy having a proximal opening at a cortical surface of the bone and a distal vertex adjacent to the bony hinge, whereby after said osteotomy is formed said proximal opening is forced apart such that said two bone portions pivot with respect to one another about said vertex, the wedge-shaped spacer comprising:
 a body having a first generally planar surface,
 a second generally planar surface,
 a proximal end,
 a distal end,
 a first lateral side and a second opposite lateral side respectively coupled between the proximal end and the distal end,
 an insertion axis to extend from the proximal end toward the distal end, and
 a lateral axis extends from the first lateral side to the second lateral side,
 the first and second surfaces being spaced further apart at a position adjacent to the proximal end than at a position adjacent to the distal end, such that a first non-zero angle is formed between said first and second surfaces in a first plane containing the insertion axis,
 the first and second surfaces being spaced further apart at a position adjacent to the first lateral side than at a position adjacent to the second lateral side, such that a second non-zero angle is formed between said first and second surfaces in a second plane containing the lateral axis; and
 at least one fixation plate extending generally orthogonally to one or both of the first and second surfaces,
 wherein said at least one fixation plate and said body are a unitary construction,
 wherein said at least one fixation plate is made of a material having properties differing from a material constituting portions of said body, said fixation plate material being relatively more malleable than said material constituting remaining portion of said body, and
 wherein said body further defines an opening extending between the first surface and the second surface and forming a gap in a proximal sidewall, said gap extending approximately half the distance from the proximal sidewall to a distal sidewall, such that said spacer is generally U-shaped, whereby bone can grow between the two bone portions at the proximal side of the osteotomy.

19. The spacer of claim 18, wherein the first plane is the coronal plane and the second plane is the sagittal plane, and the first and second angles provide a predetermined coronal plane adjustment and a predetermined sagittal plane adjustment.

20. The spacer of claim 18, wherein alignment in the coronal plane and alignment in the sagittal plane can be independently controlled.

21. A wedge-shaped spacer for insertion into a cooperating osteotomy formed in a bone, the osteotomy partially dividing the bone into two bone portions connected by a bony hinge, the osteotomy having a proximal opening at a cortical surface of the bone and a distal vertex adjacent to the bony hinge, whereby after said osteotomy is formed said proximal opening is forced apart such that said two bone portions pivot with respect to one another about said vertex, the wedge-shaped spacer comprising:
 a body having a first generally planar surface,
 a second generally planar surface,
 a proximal sidewall,
 a distal sidewall, and
 an insertion axis extending longitudinally from the distal sidewall to the proximal sidewall, the first and second surfaces being spaced further apart at a position adjacent to the proximal sidewall than at a position adjacent to the distal sidewall, such that a first non-zero angle is formed between said first and second surfaces in a first plane containing the insertion axis, the first and second surfaces being angled relative to one another in a second plane perpendicular to the insertion axis by a second angle, whereby insertion of the spacer into the osteotomy ensures that the two bone portions will be retained in desired relative positions controlled by said first and second angles;
 at least one fixation plate extending generally orthogonally to one or both of the first and second surfaces; and
 an opening extending between the first surface and the second surface to form an aperture in the proximal sidewall, said aperture extending from the proximal sidewall toward the distal sidewall, such that said spacer is generally U-shaped, whereby bone can grow between the two bone portions at the proximal side of the osteotomy,
 wherein said at least one fixation plate and said body are a unitary construction, and
 wherein said at least one fixation plate is made of a material having properties differing from a material constituting portions of said body, said fixation plate material being relatively more malleable than said material constituting portions of said body.

22. The spacer of claim 21 wherein each fixation plate includes at least one transverse hole configured to receive a bone screw.

23. The spacer of claim 21 wherein spacer comprises a bioresorbable material.

24. The spacer of claim 21 further comprising a bore being formed in the body, the bore being at least partially threaded and extending through a portion of the body from near the distal end to near the proximal end and lying between the first and second surfaces over at least a portion of the length of the bore, the spacer further comprising a threaded fastener inserted into the bore and engaging the spacer such that one end of the fastener may be mounted on the bone and threaded into the bore in the spacer to translate the spacer toward the distal vertex.

25. The spacer of claim 21, wherein the spacer body comprises a plurality of zones comprising one or more bioresorbable materials, the zones having different rates of bioresorption.

26. The spacer of claim 25 wherein the rate of bioresorption of the zones is higher for zones nearer the distal end and lower for zones nearer the proximal end of the spacer.

27. The spacer of claim 25 wherein the spacer body comprises a porous structure in which the pores are filled with one or more resorbable materials.

28. The spacer of claim 27 wherein the body comprises a porous resorbable polymer and the pores in different zones are filled with different resorbable ceramics.

29. The spacer of claim 28 wherein the resorbable polymer comprises PLLA polymer and the spacer body comprises at least three zones arranged proximally to distally, the ceramics filling the pores comprising hydroxy apatite, beta tricalcium phosphate, and calcium sulfate proximally to distally.

30. The spacer of claim 21 further comprising a bore being formed in the body, the bore to extend through a portion of the body from near the distal end to near the proximal end and lying between the first and second surfaces over at least a portion of the length of the opening, the bore extending longitudinally or transversely from the proximal end.

31. A wedge-shaped spacer for insertion into a cooperating osteotomy formed in a bone, the osteotomy partially dividing the bone into two bone portions connected by a bony hinge, the osteotomy having a proximal opening at a cortical surface of the bone and a distal vertex adjacent to the bony hinge, whereby after said osteotomy is formed said proximal opening is forced apart such that said two bone portions pivot with respect to one another about said vertex, the wedge-shaped spacer comprising:
    a body having a first generally planar surface,
    a second generally planar surface,
    a proximal end,
    a distal end,
    a first lateral side and a second opposite lateral side respectively coupled between the proximal end and the distal end,
    an insertion axis to extend from the proximal end toward the distal end, and
    a lateral axis extends from the first lateral side to the second lateral side,
    the first and second surfaces being spaced further apart at a position adjacent to the proximal end than at a position adjacent to the distal end, such that a first non-zero angle is formed between said first and second surfaces in a first plane containing the insertion axis,
    the first and second surfaces being spaced further apart at a position adjacent to the first lateral side than at a position adjacent to the second lateral side, such that a second non-zero angle is formed between said first and second surfaces in a second plane containing the lateral axis;
    at least one fixation plate extending generally orthogonally to one or both of the first and second surfaces; and
    including an opening extending between the first surface and the second surface to form an aperture in a proximal sidewall, said aperture extending from the proximal sidewall toward a distal sidewall, such that said spacer is generally U-shaped, whereby bone can grow between the two bone portions at the proximal side of the osteotomy,
    wherein said at least one fixation plate and said body are a unitary construction.

32. The spacer of claim 31, wherein the first plane is the coronal plane and the second plane is the sagittal plane, and the first and second angles provide a predetermined coronal plane adjustment and a predetermined sagittal plane adjustment.

33. The spacer of claim 31, wherein alignment in the coronal plane and alignment in the sagittal plane can be independently controlled.

\* \* \* \* \*